US008135602B2

(12) United States Patent
Xiao et al.

(10) Patent No.: US 8,135,602 B2
(45) Date of Patent: Mar. 13, 2012

(54) TECHNIQUES FOR DELIVERING COORDINATION DATA FOR A SHARED FACILITY

(75) Inventors: Yan Xiao, Gambrills, MD (US); Fu Ming (Peter) Hu, Ellicott City, MD (US); F. Jacob Seagull, Baltimore, MD (US); Colin F. Mackenzie, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1783 days.

(21) Appl. No.: 10/926,665

(22) Filed: Aug. 26, 2004

(65) Prior Publication Data

US 2005/0060211 A1 Mar. 17, 2005

Related U.S. Application Data

(60) Provisional application No. 60/498,721, filed on Aug. 28, 2003.

(51) Int. Cl.
*G06Q 10/00* (2006.01)
(52) U.S. Cl. .................. 705/7.12; 705/2; 705/3
(58) Field of Classification Search .............. 705/2, 3, 705/7, 8, 9, 7.11–7.42
See application file for complete search history.

(56) References Cited

U.S. PATENT DOCUMENTS

| | | | |
|---|---|---|---|
| 5,699,038 A * | 12/1997 | Ulrich et al. ............. | 340/286.07 |
| 6,175,954 B1 | 1/2001 | Nelson et al. | |
| 6,272,481 B1 | 8/2001 | Lawrence et al. | |
| 2002/0151990 A1 * | 10/2002 | Ulrich et al. ............. | 700/65 |
| 2002/0172498 A1 * | 11/2002 | Esenyan et al. ........... | 386/69 |
| 2003/0074222 A1 * | 4/2003 | Rosow et al. ............. | 705/2 |
| 2004/0143458 A1 | 7/2004 | Pulkkinen et al. | |
| 2005/0010441 A1 * | 1/2005 | Wheeler .................... | 705/2 |

OTHER PUBLICATIONS

Feiner, Steven and Shamash, Ari, Hybrid User Interfaces: Breeding Virtually Bigger Interfaces for Physically Smaller Computers, Nov. 11-23, 1991, UIST'91, Hilton Head, South Carolina.
Abowd, ACM transactions on Computer-Human Interaction, Mar. 2000, p. 29-58, vol. 7, No. 1.
Benford, ACM transactions on Computer-Human Interaction, Sep. 1998, p. 185-223, vol. 5, No. 3.
Cohen, Logjam: a tangible multi-person interface for video logging, CHI 99, p. 15-20, May 1999.

(Continued)

*Primary Examiner* — R. David Rines
(74) *Attorney, Agent, or Firm* — Evans & Molinelli, PLLC; Eugene Molinelli

(57) ABSTRACT

Techniques for delivering data for coordinating multiple party use of a facility include producing conditions data by measuring without human intervention current condition of a facility that is used by multiple human parties. Availability data that indicates present or future availability for the facility is generated based at least in part on the conditions data. Coordination data based at least in part on the availability data is presented for the parties. These techniques allow rapid dynamic adaptation to changing status of a high-value facility while being less reliant on varied and subjective human motivations for reporting status changes. Undue exposure of sensitive information can be avoided by deriving less detailed views from high-resolution images of the facility and its users. Coordination data can be projected directly onto, and manual input can be derived from, a magnetic white board currently used for coordination at many facilities.

20 Claims, 13 Drawing Sheets

OTHER PUBLICATIONS

McGee, Minneapolis, Minnesota, Association for Computing Machinery, CHI 2002, Apr. 20-25, vol. No. 1, Issue No. 1, p. 407-414.
Harrison, CHI 98 Los Angeles, CA, Squeeze me, hold me, tilt me! An exploration of manipulative use interfaces, p. 17-24 Apr. 1998.
Koike, ACM transactions on Computer-Human Interaction, p. 307-322, vol. 8, No. 4.
Rekimoto, Augmented Surfaces: A Spatially Continuous Work Space for Hybrid Computing Environments, CHI 99, May 15-2, p 378-385.
Jacob, A tangible interface for organizing information using a grid, Proceedings of CHI 2002, Apr. 20-25, ACM Press.
Rekimoto, CHI 2001, Mar. 31-Apr. 5, p. 269-276, 2001.
Druin, CHI 99, Pittsburg, PA, May 15-20, 1999, p. 326-329.
Ishii, CHI 97, Mar. 22-27, 1997, p. 234-241.
Schafer, A new approach to human-computer interaction—synchronous modelling in real and virtual spaces, ACM 1999, p. 335-344.
Brereton, CHI 2000, Apr. 1-6, 2000, CHI letters vol. 2., Issue 1, p. 217-224.
MacKay, CHI 1995 Mosaic of Creativity, May 7-11, p. 421-422.
Dourish, CSCW 1992 proceedings, Nov. 1992, p. 107-114.
Streitz. CHI 1998, Apr. 18-23, p. 273-274.
Want, CHI 99, Pittsburgh, PA, May 15-20, 370-377.
Plesniak, CHI 98, Los Angeles, CA, Apr. 18-23, p. 304.
No author, Collaboration around a tabletop display: supporting interpersonal interactions.
Tandler, ACM 2001, USIT'01 Letters, Orlando, Florida, p. 11-20.
Rekimoto, Cyber Code: designing augmented reality environments with visual tags, p. 1-10.
Moran, USIR 1999 Asheville, NC, CHI letters vol. 1, 1, p. 197-206.
Resmick, CHI 1998, Los Angeles, CA, Apr. 18-23, p. 281.
Ullmer and Ishii, IBM Systems journal vol. 39, Nos. 3&4, 2000, p. 915.
Guimbretiere, Fluid interaction with high-resolution wall-size displays, 1-10.
Dourish, ACM 1999, Getting some perspective- using process descriptions to index document history. Group 99, Phoenix, AZ, p. 375-384.
Matsushita, UIST 97, Banff, Alberta, Canada, ACM 1997, HoloWall: designing a finger, hand, body and object sensitive wall. p. 209.
Streitz, CHI 99, May 15-2, p. 120-127.
Wellner, Interacting with paper on the digital desk, ACM 1993 vol 36. No. 7 p. 87.
McCullough, Human-Computer Interaction, 2001 vol. 16, p. 337-349.
Pedersen, ACM 2000, Paper Buttons: expanding a tangible user interface, p. 216-223.
Harper, Tech Report EPD 1995-109, Paper supported collaborative work.
Moran, UIST 1997, Banff, Alberta, Canada, ACM 1997, Pen-based interaction techniques for organizing material on an electronic whiteboard, p. 45-54.
Greeenberg, ACM UIST 2001 Symposium on user interface software and tech. Nov. 11-14, Orlando, Florida.
Ishii, CHI 99, Pittsburg, PA, May 15-20, p. 394.
Dourish, Human-Computer Interaction 2001 vol. 16, p. 229-241.
Patten, CHI 2001, Mar. 31-Apr. 5, ACM Press.
Pawlowski, Supporting shared information systems: boundary objects, communities and brokering, p. 329-338.
Brave, CSCW Seattle, Washington, ACM 1998, Tangible interfaces for remote collaboration and communication, p. 169-178.
Schkolne, CHI 2003, Tangible + Virtual = a flexible 3D interface for spatial construction applied to DNA.
Stifelman, CHI 2001, Mar. 31-Apr. 5, vol No. 3, Issue No. 1. p. 182.
Klemmer, UIST 2001 Orlando Florida, ACM 2001, The designers' outpost: a tangible interface for collaborative web site design, Nov. 11-14, 2001, p. 1-10.
Blaine, DIS 2000, ACM, p. 165, The jam-o-drum interactive music system: a study in interaction design.
Wrensch, UIST 1998, San Francisco, CA, ACM, The programmable hinge: toward computationally enhanced crafts, 89-96.
Rekimoto, UIST 1995, The world through the computer: computer augmented interaction with real world environments, Nov. 14-17, p. 29.
Crowley, Mar. 2000, vol. 43, No. 3, Communications of the ACM, p. 54-64.
Yarin, CHI 1999, May 15-20, p. 362.
MacKay, ACM 1994, Video Mosaic: laying out time in a physical space.
Ljungstrand, Designing augmented reality environments, 2000, Elsinore, Denmark, Apr. 12-14, 2000/.

\* cited by examiner

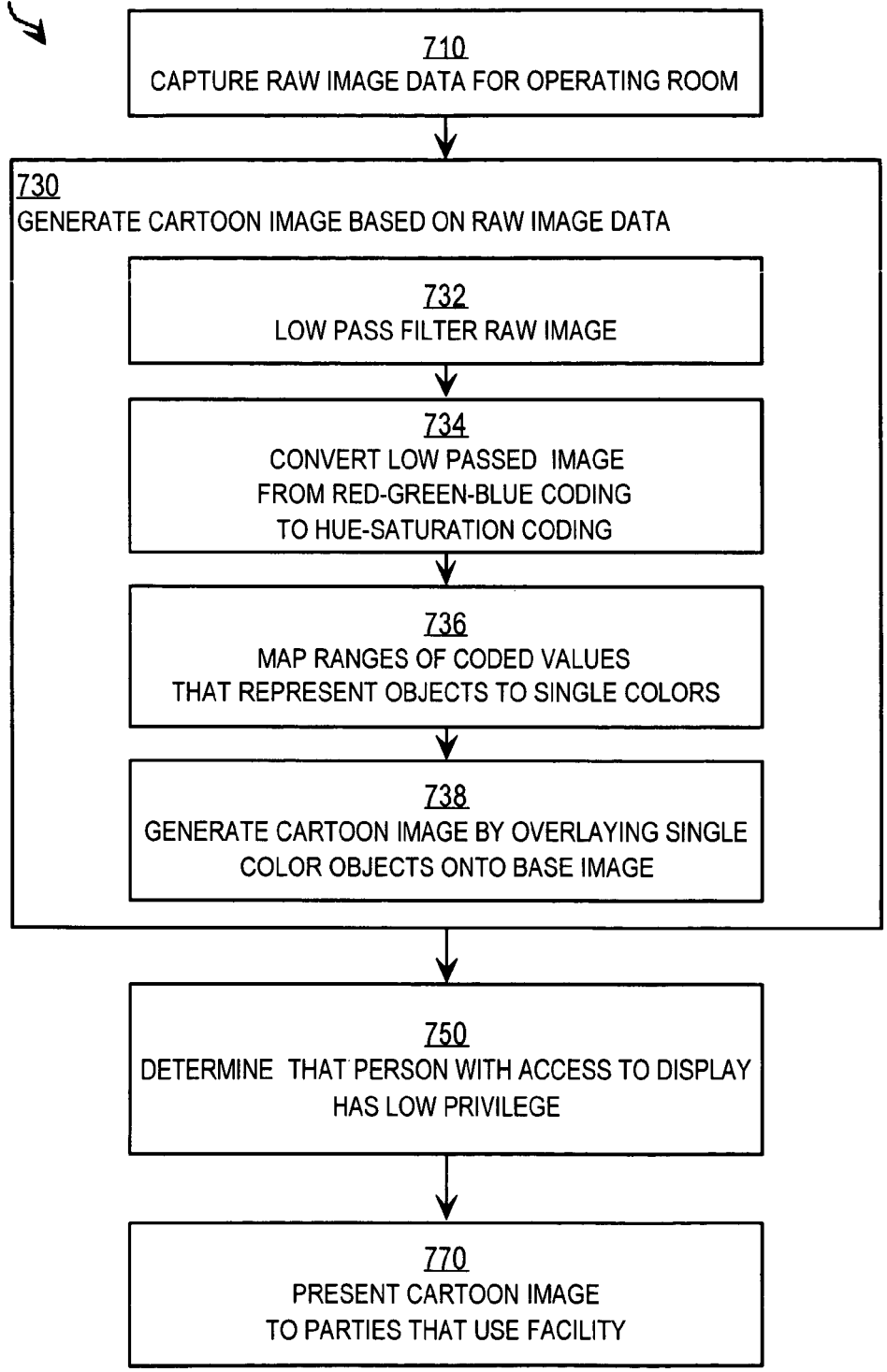

780 DETAILED VIEW 781a  781b  782a  782b  783  782c  781c
       784a  784b

790 CARTOON VIEW 794b  793

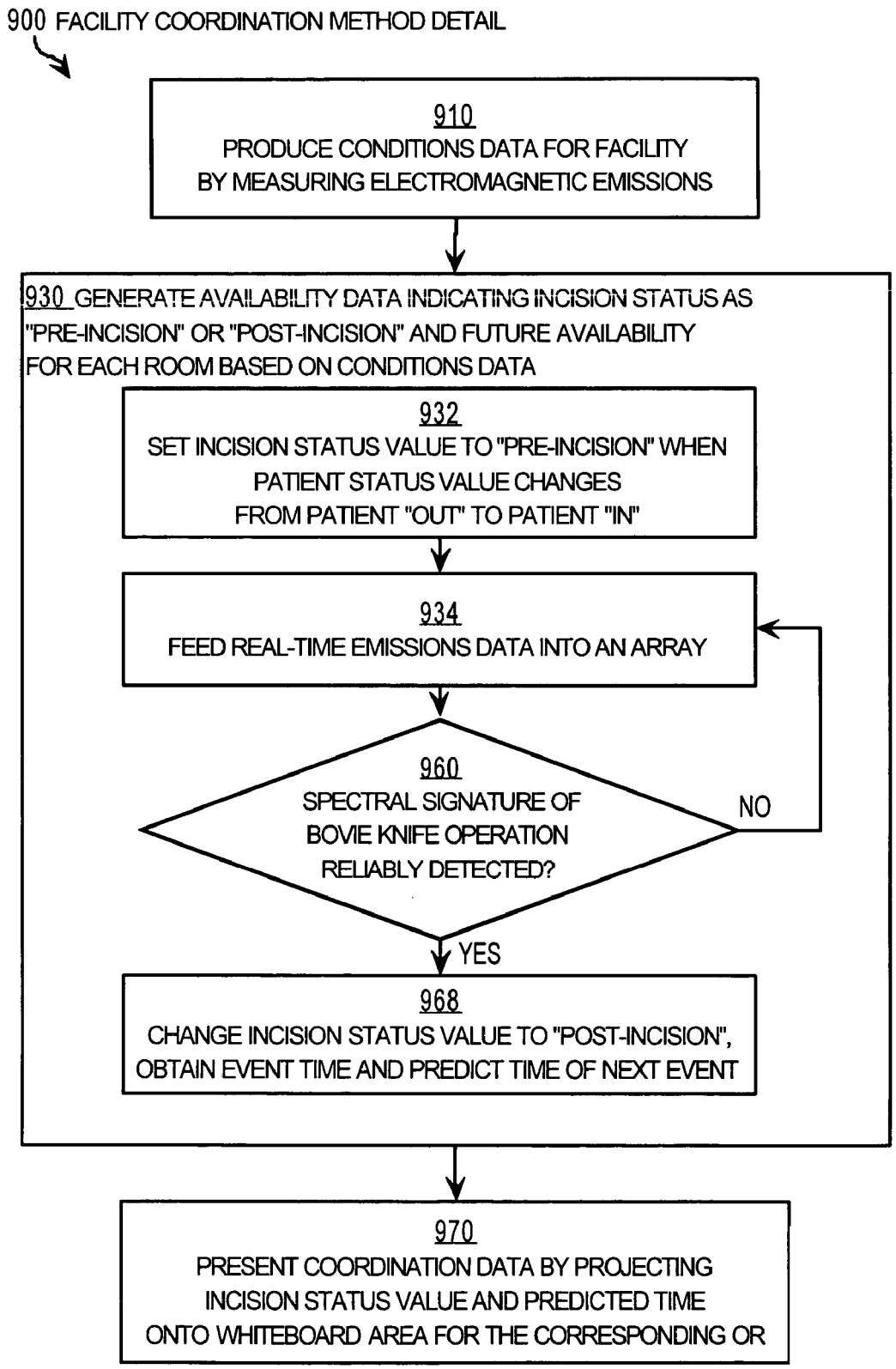

TECHNIQUES FOR DELIVERING COORDINATION DATA FOR A SHARED FACILITY

CROSS-REFERENCE TO RELATED APPLICATIONS

This application claims benefit of Provisional Appln. 60/498,721, filed Aug. 28, 2003, the entire contents of which are hereby incorporated by reference as if fully set forth herein, under 35 U.S.C. §119(e).

STATEMENT OF GOVERNMENTAL INTEREST

This invention was made with Government support under Contract No. 9900406 awarded by the National Science Foundation and Contract No. 02129002 awarded by the Telemedicine and Advanced Technology Research Center (Department of the Army). The Government has certain rights in the invention.

BACKGROUND OF THE INVENTION

1. Field of the Invention

The present invention relates to systems for coordinating the use of a high valued facility among many persons, and in particular to measuring conditions and deriving availability parameters without human intervention for integrated display, such as on a magnetic whiteboard with manually entered information.

2. Description of the Related Art

Hospital operating rooms (ORs) are valuable facilities. It has been estimated that in typical hospitals, the operating rooms account for about 40% to about 50% of revenue from patients. The operating rooms also account for a large share of the hospital resources and expenses. It is in the interest of the hospital administrators to make maximum use of the operating rooms in their hospital, such as by minimizing the time from the exit of one patient to the entry of the next patient. However, the use of each operating room in the hospital requires the coordinated efforts of a large number of persons or teams of persons, including for example, surgeons, anesthesiologists, surgical assistants, charge nurses, cleaning staff, equipment maintenance staff, and runners who bring patients and supplies into and out of the operating room. Each person or team must often complete the person's or team's own task before another person or team can use the facility.

For example, after a procedure on a patient is completed, the following sample actions may take place in sequence: the patient is prepared for removal by anesthesiologists and nurses, for example by disconnecting the patient from anesthesia delivery equipment and covering the patient; the patient is removed from the operating room by an anesthesia care provider; and the operating room and its operating table are cleaned by cleaning staff. Before the next procedure can begin, the following sample actions may take place in sequence: the cleaned operating room and table are prepared for the next patient by OR nurses and technicians; equipment and tools to be used in the next procedure are brought in, serviced or repaired by equipment maintenance staff; supplies are replenished by support staff; the next patient is brought in and transferred to the operating room table by nurses and anesthesia care providers; and the next patient is prepared for the procedure, for example, by receiving anesthesia from an anesthesiologist and by being connected to a fixed or mobile heart and blood oxygen level monitoring equipment by a OR nurse. Only then may the surgeon begin the next procedure. Charge nurses for surgical operating rooms connect multiple people, resources, and patients to ensure efficient and safe operation of the operating room. The various persons, alone or in teams, are often standing by—ready to act when the room or patient is in a state to be acted upon.

The sequencing of actions by these personnel would be relatively easy to plan and execute if all procedures in an operating room were predictable with certainty. However, procedures performed in operating rooms can deviate in both number and temporal duration substantially from average or planned use. In contrast to most operating rooms, day-of-surgery case scheduling in a trauma center is especially dynamic. Much of the decisions on surgical case scheduling in trauma centers are made on the day of surgery, whereas in most other operating rooms the scheduling is usually determined days in advance. In either case, persons who act in the operating room are unable to determine exactly when their services are required. As a consequence, resources are wasted as person wait idly by for an operating room that is not ready for their activity, or are occupied in another operating room or area when their action is required next in a different operating room. For example, if a procedure finishes half an hour early, a doctor en route for the next operation expected to start at 10 AM may be unavailable when the room is ready. Thus valuable minutes of operating room availability are lost.

A charge nurse takes requests for surgery and translates them into a schedule of specific times or sequences, or both, in each of the individual operating rooms (e.g., six operating rooms in an illustrated example). If a case is not scheduled as the first case, its starting time cannot be accurately scheduled. The order of the case is then scheduled "to follow" the first case for the respective operating room. Charge nurses are attired in "scrubs" (sterile gloves and gown) typically to go inside the operating rooms. They do not have clinical duties ordinarily, although they often have extensive clinical experience working in the operating rooms. The charge nurses are mobile during their shift and do walk around; but the charge nurses primarily remain in the vicinity of a control desk typically located in or near a corridor through which surgical patients are brought in.

Examples of changes affecting the planned surgery schedule include cancelled surgeries; unexpected additional surgeries (which result from both newly admitted patients as well as deterioration of previously admitted patients necessitating re-visits to an operating room); multi-patient trauma situations in which demand exceeds resource supply, at least temporarily; and any external variables impacting operating room operational status (unavailable or malfunctioning equipment, lack of supplies, and changes in staffing patterns, such as caused by illness, attrition, and hiring delays).

Based on reports of patient exit from an operating room and next patient entry into the operating room, operating room use efficiency can be measured and compared. One measure of operating room (OR) efficiency is the percentage of operations that start on time—so called "on-time OR starts." The industry average for on-time OR starts is 27%. The best performing operating rooms have on-time OR starts of 76%. Clearly, there is room for improvement at all hospitals.

In one approach, employed for a suite of operating rooms that exhibit good performance, the charge nurses use a large whiteboard (365×122 cm) in front of the control desk. The whiteboard is used in part to show surgical schedules. Different portions of the whiteboard are devoted to different operating rooms. A magnetic strip with case information is prepared for every case scheduled for the suite of operating rooms. The magnetic strips are arranged or updated to indicate the current status of the case, including the operating room where the case is to be handled and the sequence of the cases in that operating room and the state of readiness of the patient associated with the case. Other details can be written into the spaces on the whiteboard or the magnetic strips with markers, or typed or written on papers taped to the whiteboard. Magnetic strips or tokens are also prepared for various staff and positioned on the whiteboard according to their availability and assignment.

While providing a useful place for recording and exchanging information about the use of the operating rooms, the whiteboard has some shortcomings. Updating the whiteboard requires human interaction. Thus the whiteboard is subject to failures when information is not provided by the human users. For example, a human might not report new information due to forgetfulness; distraction by personal, emotional or urgent events; physical separation from the whiteboard; or motivation to delay reporting information (for example, to prevent the early termination of a rest break or meal break or to delay reporting an unusual absence by a favored coworker).

In another approach, video cameras and microphones were installed in surgical operating rooms to relay audio and video to remotely situated neurophysiologists. Prior to this approach, those neurophysiologists could access patient monitoring data remotely. With the addition of audio and video, the neurophysiologists could monitor the patient better by the supplemental audio and video information about the progress of a surgery and estimate when a procedure might likely be completed. Additionally, neurophysiologists could schedule their tasks better by utilizing low-workload periods better.

While improving the availability of information about the current use of a facility, the approach of transmitting video and audio was found to raise serious privacy issues, such as casual conversations in operating rooms being overheard by those remotely situated. In particular, participants were inhibited by the possibility of their work activities being broadcast to unseen and unknown observers.

Furthermore, while experienced neurophysiologists could determine a stage of a procedure by observing the video and audio data, other personnel using the facility were not appraised of the progress of the procedure or warned when a procedure was completed or a patient was being prepared for removal or given estimates of when their next action would likely be required. Thus other personnel still had to guess when they should report for their next action, wasting resources when they guessed incorrectly.

Clearly there is a need for a system to share status and availability information about operating rooms that does not suffer the disadvantages of previous approaches, such as subjective updating, loss of privacy and discretion, and lack of predictions for the time of subsequent actions for all concerned staff, among other deficiencies.

In general, there is a need for a system to share status and availability information about other high value facilities that are used by multiple persons in a coordinated interaction that does not suffer the disadvantages of previous approaches.

SUMMARY OF THE INVENTION

Techniques are provided for delivering data for coordinating multiple party use of a facility. These techniques remove one or more deficiencies of previous approaches, and can improve the efficient use of high valued facilities such as hospital operating rooms and emergency response resources.

In one set of embodiments, a method for delivering data for coordinating multiple party use of a facility includes producing conditions data by measuring without human intervention a current condition of a facility for which use is coordinated among multiple human parties. Availability data that indicates availability for the facility is generated based at least in part on the conditions data. Coordination data based at least in part on the availability data is presented for all the parties. These embodiments improve information flow by reducing reliance on subjective human input and providing information to all parties whose uses of the facility are to be coordinated.

In some embodiments of this set, the facility includes one or more trauma center operating rooms, surgical operating rooms, emergency room suites and cardiac catheterization laboratories, and the parties include medical doctors, nurses, medical technicians and orderlies.

In some embodiments of this set, the method further includes determining a party who has access to the coordination data at a particular time and a particular level of privilege associated with that party. The step of generating the availability data includes generating sensitive data and multiple views of the sensitive data with different levels of detail. A particular view is omitted from the coordination data based on the particular level of privilege of the party with access. These embodiments help protect privacy when utilizing highly revealing measurements of facility conditions.

In some embodiments of this set, the conditions data collected includes images of the facility. In some of these embodiments, generating availability data includes deriving from the image data a cartoon view with a solid filled shape to represent an object in the image data. The cartoon view is presented with the coordination data instead of the more detailed images of the facility.

In some embodiments of this set, generating availability data includes deriving from the conditions data a status value among multiple status values for one or more status parameters, such as table status parameter, patient status parameter, operating room activity status parameter, and an incision status parameter.z In some embodiments of this set, schedule data that indicates a planned use for the facility is also received and the coordination data includes a display element that indicates a deviation from the planned use.

In another set of embodiments, a method for reducing image detail to protect sensitive information includes capturing an original image and low pass filtering it. A range of colors in the low passed image associated with a feature in the original image is mapped to a single color. A low detail "cartoon" image is generated with the single color at each location where a color of the low passed image falls within the range of colors.

In another set of embodiments, a method for presenting data representing actual use of a facility includes presenting a first bar that indicates time for planned use of a facility. A second bar is presented for elapsed time of actual use of the facility, which extends at least in part outside the first bar.

In another set of embodiments, a method for inputting data to a computer connected to a video input includes capturing a video image of a two dimensional surface including a manually positioned tangible token. Either a location or an orientation of the tangible token, or both, indicates one state among more than two possible states. A particular state of the possible states is determined based on the video image.

In other sets of embodiments, computer-readable media and systems perform the methods described above.

BRIEF DESCRIPTION OF THE DRAWINGS

The present invention is illustrated by way of example, and not by way of limitation, in the figures of the accompanying drawings and in which like reference numerals refer to similar elements and in which:

FIG. 7A is a flow diagram that illustrates a facility coordination method using sensitive image data, according to an embodiment;

FIG. 9 is a flow diagram that illustrates a facility coordination method using non-intrusively measured equipment operation data, according to an embodiment;

DETAILED DESCRIPTION

A method and apparatus are described for delivering data for coordinating multiple party use of a facility. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

In particular, embodiments of the present invention are described in the context of a whiteboard display in a control area of a suite of hospital operating rooms (including trauma center operating rooms or surgical operating rooms or both); however the invention is not limited to this context. Other embodiments of the invention are employed in other medical facilities, such as patient scanning and imaging laboratories, cardiac catheterization laboratories, emergency rooms, and veterinary facilities. Other embodiments of the invention are employed for facilities beyond the scope of a single hospital, such as emergency response facilities distributed among several hospitals, government buildings and mobile units (such as ambulances, fire trucks, rescue boats) utilized by emergency response personnel such as policemen, firemen, Coast Guard personnel, National Guard personnel and regular military personnel. Other embodiments of the invention are employed for non medical facilities used by multiple parties, such as aircraft utilized by various personnel such as aircraft preparation personnel including mechanics, baggage handlers, caterers, cleaning crew and a flight crew, and security staff, among others.

Figure 1:
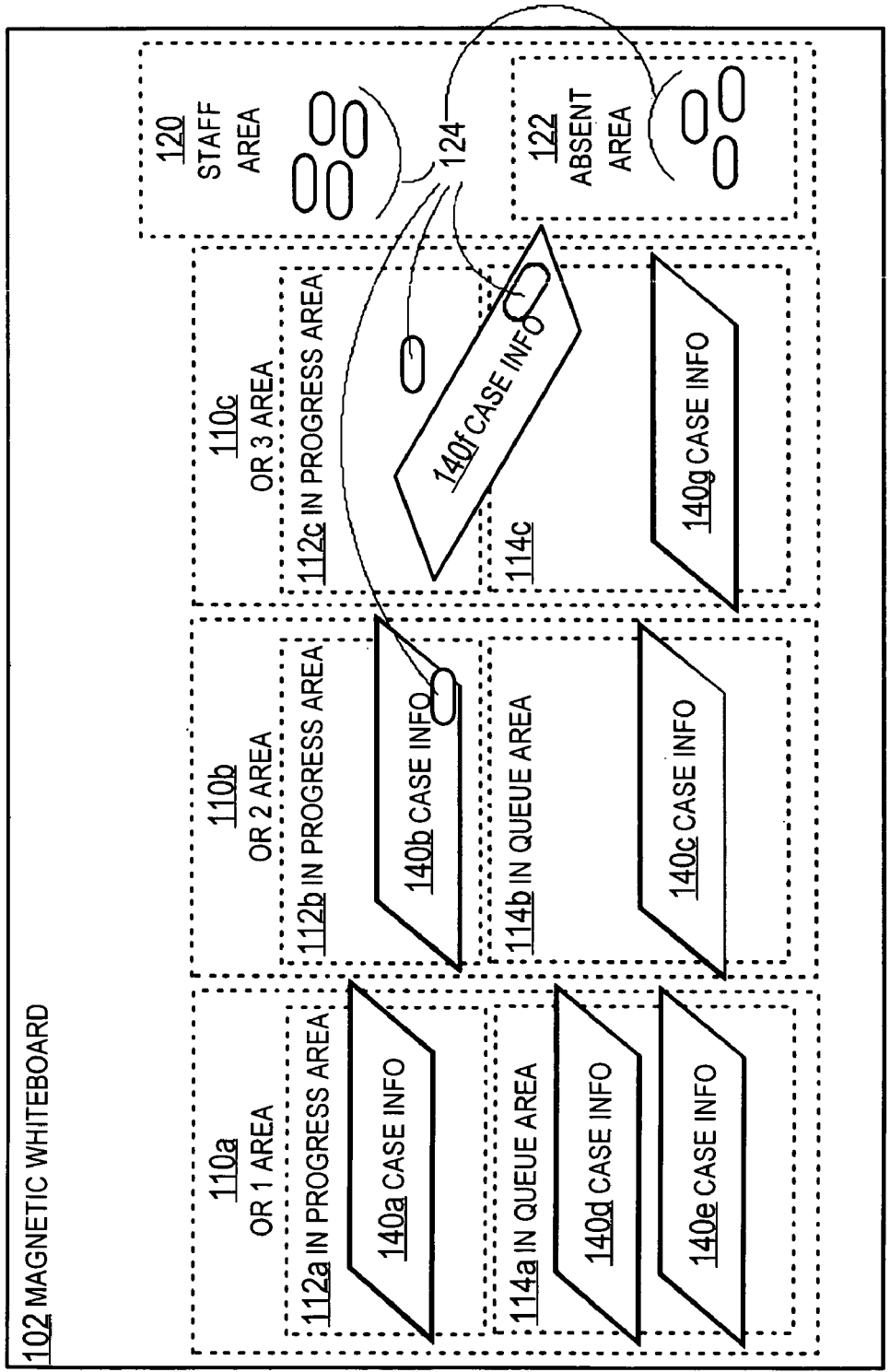
FIG. 1 is a block diagram that illustrates a facility coordination system based on human input.

The generation and use of coordination data is illustrated for an approach using a centrally located whiteboard. FIG. 1 is a block diagram that illustrates a facility coordination system 100 based on human input to a magnetic whiteboard 102. The whiteboard 102 is magnetic in the sense that magnetic objects will adhere to the whiteboard. Embodiments of the invention are not limited to a centralized magnetic whiteboard for display of coordination data or user input or both, but may use any centralized or distributed input/output (I/O) system to display coordination data or to receive user input or both.

Whiteboard 102 is divided into different areas corresponding to different operating rooms within the purview of the control desk. In the illustrated example, whiteboard 102 is divided into areas 110a, 110b, 110c corresponding to operating rooms OR 1, OR 2, OR 3, respectively. Each of these operating room areas 110a, 110b, 110c is further divided into an "in progress" area 112a, 112b, 112c (collectively referenced herein as in progress areas 112) and an "in queue" area 114a, 114b, 114c (collectively referenced herein as in queue areas 114), respectively. The in progress areas 112a, 112b, 112c are reserved for information related to cases that are in progress in the corresponding operating room OR 1, OR 2, OR 3, respectively. The in queue areas 114a, 114b, 114c are reserved for information related to cases that are in line to be handled in the corresponding operating room OR 1, OR 2, OR 3, respectively. Whiteboard 102 is further divide into a staff area 120 where information related to operating room personnel is maintained. The staff area is further divided into an absent area 122 and a non-absent area. The absent area is reserved for information about staff members who are not available to perform actions in the operations rooms OR 1, OR 2, OR 3. In other hospitals a whiteboard may be divided into more or different areas.

Magnetic objects are attached to the whiteboard 102. For example, magnetic personnel objects 124 are attached for each person on the staff for the operating rooms. In some embodiments, the name of a staff member is printed or hand written on a magnetic personnel object 124. Magnetic case strips 140a, 140b, 140c, 140d, 140e, 140f, 140g, collectively referenced herein as magnetic case strips 140, are attached for cases to be processed through one of the operating rooms OR 1, OR 2 and OR 3. Case information, such as case number, responsible doctor, type of operation, and description of the patient or procedure, is printed or hand written onto the magnetic case strips 140.

Staff members who are currently not available for actions in the operation rooms OR 1, OR 2, OR 3 are represented by magnetic personnel objects 124 in the absent area 122 of staff area 120. Staff members who are available for actions in the operation rooms OR 1, OR 2, OR 3 are represented by magnetic personnel objects 124 in the staff area 120 outside of the absent area 122. Staff members currently assigned to an operating room are represented by magnetic personnel objects in an OR area, such as magnetic personnel objects 124 in in progress areas 110b, 110c in FIG. 1. Staff members currently assigned to a particular case are represented by magnetic personnel objects on a case strip, such as magnetic personnel object 124 on case strip 140f in FIG. 1. Other information related to staffing may be written manually with whiteboard markers or printed and taped to the corresponding staff areas 120, 122 of the whiteboard 102.

Cases currently in progress in an operating room are represented by magnetic case strips 140 in the in progress area 112 of operating room area 110. In the illustrated embodiment, magnetic case strips 140a in area 112a holds information related to the case currently in progress in OR 1; and magnetic case strips 140b in area 112b holds information related to the case currently in progress in OR 2. Cases scheduled for an operating room are represented by magnetic case strips 140 in the in queue area 114 of operating room area 110. In the illustrated embodiment, magnetic case strips 140d, 140e in area 114a hold information related to the next two cases scheduled for OR 1; magnetic case strip 140c in area 114b holds information related to the next case scheduled for OR 2; and magnetic case strip 140g in area 114c holds information related to the next case scheduled for OR 3. Other information related to each OR or the cases scheduled for each OR may be written manually with whiteboard markers or printed and taped to the corresponding areas of the whiteboard 102.

The whiteboard and magnetic objects are easily manipulated by humans and can be adapted to provide other or subtle nuances in information. For example, magnetic case strip 140f is positioned to substantially overlap both the in progress area 112c and the in queue area 114c for OR 3 to indicate that the patient for this case is currently being prepared for the OR procedure. Perhaps the patient is in the room and waiting to be connected to the vital signs monitors or anesthesia equipment, so the case is not yet in progress, but is more advanced than a case for which the patient is still in a holding room. Whether the left side or the right side of the magnetic case strip 140f is in the in progress area 112c may be used to further distinguish the degree of readiness to proceed with the case. A magnetic personnel object 124 placed on case strip 140f may indicate a runner responsible for moving the patient for the case from a staging or holding room into the operating room, or a nurse responsible for connecting the patient to the vital signs monitor.

As described in the previous section, a system like the one depicted in FIG. 1 has many useful features. However, it suffers from a reliance on human input that is subjective and subject to oversight, error, or hidden motivations.

1. Functional Overview

Figure 2:
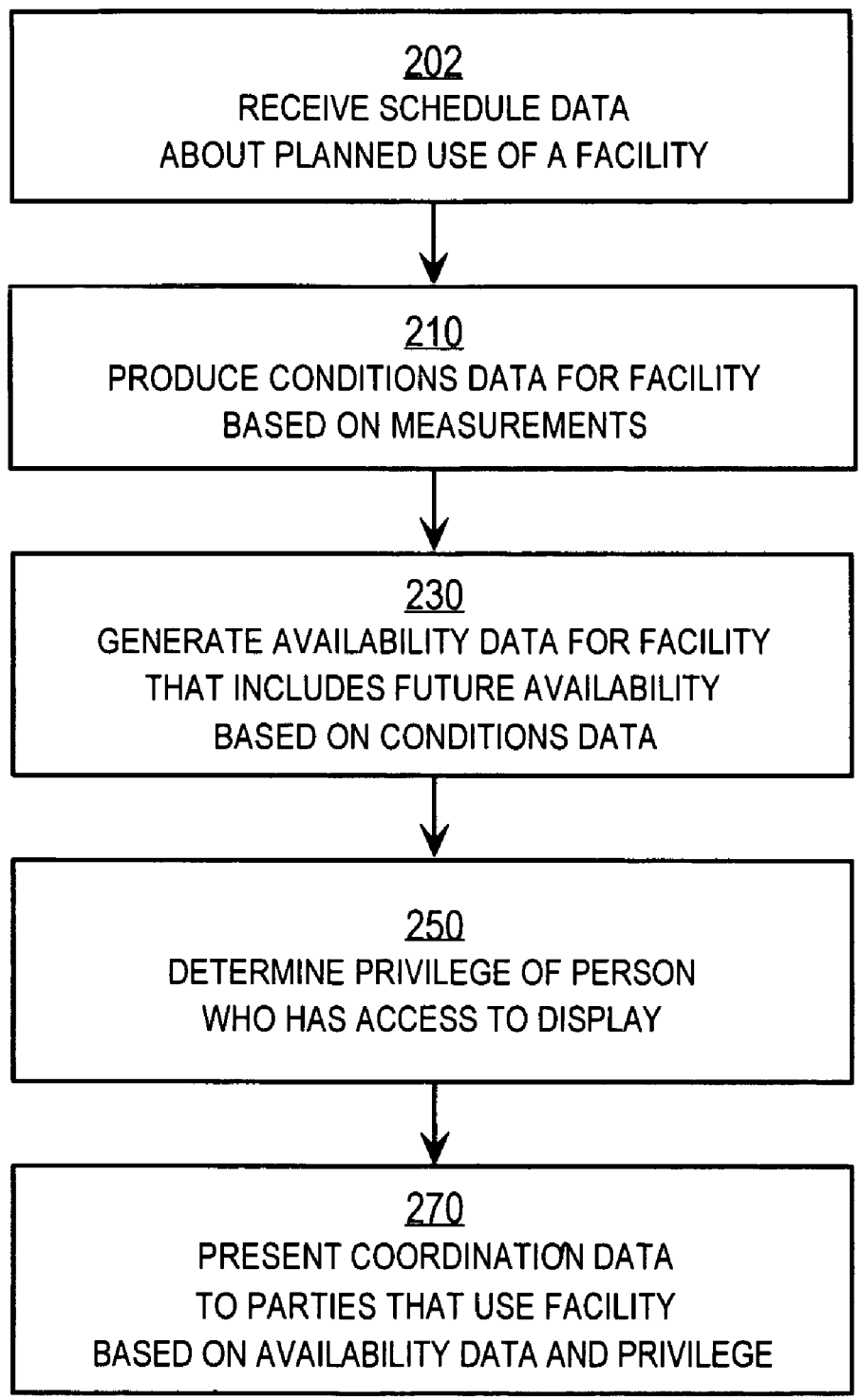
FIG. 2 is a flow diagram that illustrates at a high level a facility coordination method, according to an embodiment.

FIG. 2 is a flow diagram that illustrates at a high level a facility coordination method 200, according to an embodiment. Although steps in FIG. 2 and subsequent flow diagrams are presented in a particular order for purposes of illustration, in other embodiments one or more steps may be performed in a different order, or may overlap in time, or may be omitted. For example, in FIG. 2, step 202 is omitted in some embodiments, overlaps steps 210 or 230 in some embodiments, and is performed after step 210 in some embodiments.

In step 202, planned use of the facility is obtained. This information is obtained so that actual use deduced from steps described below can be compared to the planned use; and alerts may be sent if the actual use deviates too far from the planned use. For example, in some embodiments of step 202, schedule data is received from a scheduling database for a facility. Many facilities use computer applications called scheduling systems to manage schedules of persons or facilities or both. Such computer applications often use a central or distributed database with information about planned use of a facility. In an illustrated embodiment, charge nurses use a facility scheduling system to enter, hours or days ahead, information about planned used of the facility, such as, for each operating room in their facility, a date, a start time, or a sequence of cases to be performed, or some combination. In some embodiments, the expected duration time for the case based on statistics of prior cases of the same type may be entered. In some embodiments, a database is not used and step 202 includes deriving operating room, date, start time, and sequence of cases using optical character recognition (OCR) computer applications operating on data written onto a whiteboard or magnetic strips attached to the whiteboard. In some embodiments, step 202 is omitted and no planned use is input to the system.

In step 210, conditions data is produced based on measurements of the facility. At least some of these measurements are automatic and do not depend on human input. Human input, when available may also be used in step 210. For example, data from equipment in the operating rooms is collected. In some embodiments, sound and still or video data, or some combination, is also collected during step 210. For example, one or more video cameras are installed in each operating room and holding room and image data is collected. These embodiments improve information flow by reducing reliance on subjective human input.

In step 230, the data collected in step 210 is used to determine availability of the facility and produce availability data to describe that availability. Availability of the facility includes deductions of current status or predictions of status at particular times in the near future, or both. For example, in some embodiments, availability data is produced that indicates an operating room table is empty since a time two minutes earlier based on image processing of a sequence of video images of the operating room. In some embodiments that include predictions, availability data is produced that indicates an operating room table is empty since a time two minutes earlier and will become ready for the next patient at a time three minutes in the future. Such predictions may be performed using any known method; for example, using statistics of the average delay between a table becoming empty and first becoming ready for the next patient, for a particular operating room, suite of operating rooms, or industry averages. In some embodiments, the present or predicted status is accompanied by a measure of precision of the status, such as a probability of accuracy for table conditions derived from images or the standard deviation of delays about the average delay between empty status and ready status.

For example, in some embodiments, the availability data generated in step 230 includes producing an operating table (also called an operating room bed) status. In this embodiment, the values for the operating room table status are "empty," "ready," "patient on the table," "drapes-off," "drapes-on," and "drapes off, after-on." The "empty" status value indicates an operating room table is not occupied and is not prepared for a new occupant. The "ready" status value indicates the operating room table is not occupied and is prepared for new occupant. The "patient on the table" status value indicates the patient is on the OR table. The "drapes-off" status value indicates the operating room table is occupied and the occupant is not covered with a surgical drape. The "drapes-on" status value indicates the operating room table is occupied and the occupant is covered with a surgical drape. Surgery is performed only after a surgical drape is positioned over the patient. The "drapes off, after-on" status value indicates surgery close to the end and patient is getting ready to be moved out of the OR.

The status value is determined in step 230 by image processing of camera images that depict the operating room table. Based on color and texture data derived for locations associated with the known position of the table, and subtracting out the effects of people moving in the operating room between the camera and the table, the status can be usefully detected. For example, in some embodiments the live video images of red, green, blue values for each pixel (RGB code) or hue, level of saturation and brightness values (HSV code) are used with inter-image variance compensated for lighting changes to identify the "empty status." Edge detection routines (such as available in MATLAB of MathWorks, Natick, Mass.) are used to determine the size and orientation of the table, and texture characteristics deduced from RGB or HSV histogram value ranges in the table location are compared with the previous texture characteristics obtained from bed ready conditions to identify the "ready" or "not ready" status values. "Drapes-on" or "drapes-Off" status is determined in some embodiments by identifying the bed area first, then comparing the standard drape texture and color with the values in the bed area. For example, in a sequence of test derivations, the image processing procedure correctly identified the "empty" status 76% of the time, the "ready" status 80% of the time, the "drapes-on" status 67% of the time and the "drapes-off" status 57% of the time.

In embodiments that include step 202, availability of the facility includes information about how far the actual status deviates from planned use. For example, availability data is produced that indicates the operating room table is ready for the next patient as of a certain time that is eight minutes later than the planned time for that operating room table to be ready.

In some embodiments, the data collected in step 210 is considered sensitive and not for general consumption among all parties that coordinate use of the facility. For example, full resolution video images of the operating room during a procedure or preparation for a procedure are considered sensitive. In such embodiments, step 230 includes producing one or more less detailed views of the sensitive data, such as a lower resolution image one fourth (¼) the height and width of the full resolution picture and having one sixteenth (1/16) the number of pixels and no audio, or cartoon images described in a later section.

In step 250, the privileges of persons who have current access to data displays are determined. For example, in various embodiments, a user types in a personal identification number (PIN) at a keypad; a user swipes an identification (ID) card through a card reader or shows the ID card to a camera; or a user gives a sample to a detector for a system that identifies a human based on a unique physical characteristic such as a fingerprint, handprint, or retinal image. In some embodiments all parties who have access to displayed data may view any data collected and displayed; in such embodiments, step 250 may be omitted.

In step 270 coordination data based on the availability data is made available to all parties. For example, not just surgeons, but anesthesiologists, nurses, orderlies, runners, technicians and others whose use of the facility is coordinated may view the coordination data. These embodiments improve information flow by providing information to all parties whose use of the facility are to be coordinated. In some embodiments, the coordination data includes only views of sensitive data that depend on the persons having access to the coordination data at a particular time. For example, if a person with high levels of privilege has been identified as having current access in step 250, then a high detailed view of the sensitive data is displayed for a short period of time. In some embodiments, it is assumed as a default condition that all persons have access to the display and only the low detailed views for the lowest levels of privilege are displayed. If a person with a higher level of privilege is detected, then a view with greater detail is displayed. In some embodiments, the greater detail is displayed automatically when the person with higher privilege indicates his or her presence. In some embodiments, the person with higher privilege must also indicate a desire for the greater detail view, such as by keying input or moving a token on the whiteboard.

In some embodiments the system includes a communication link to a remote site. In such embodiments, step 270 includes forming a remote display image based at least in part on an image of the coordination board (such as an image of the white board 102 and the magnetic elements on it) and the coordination data. Step 270 also includes sending the remote display image over the communications link to a remote display device at the remote site for displaying the remote display image.

2. Structural Overview

Figure 3:
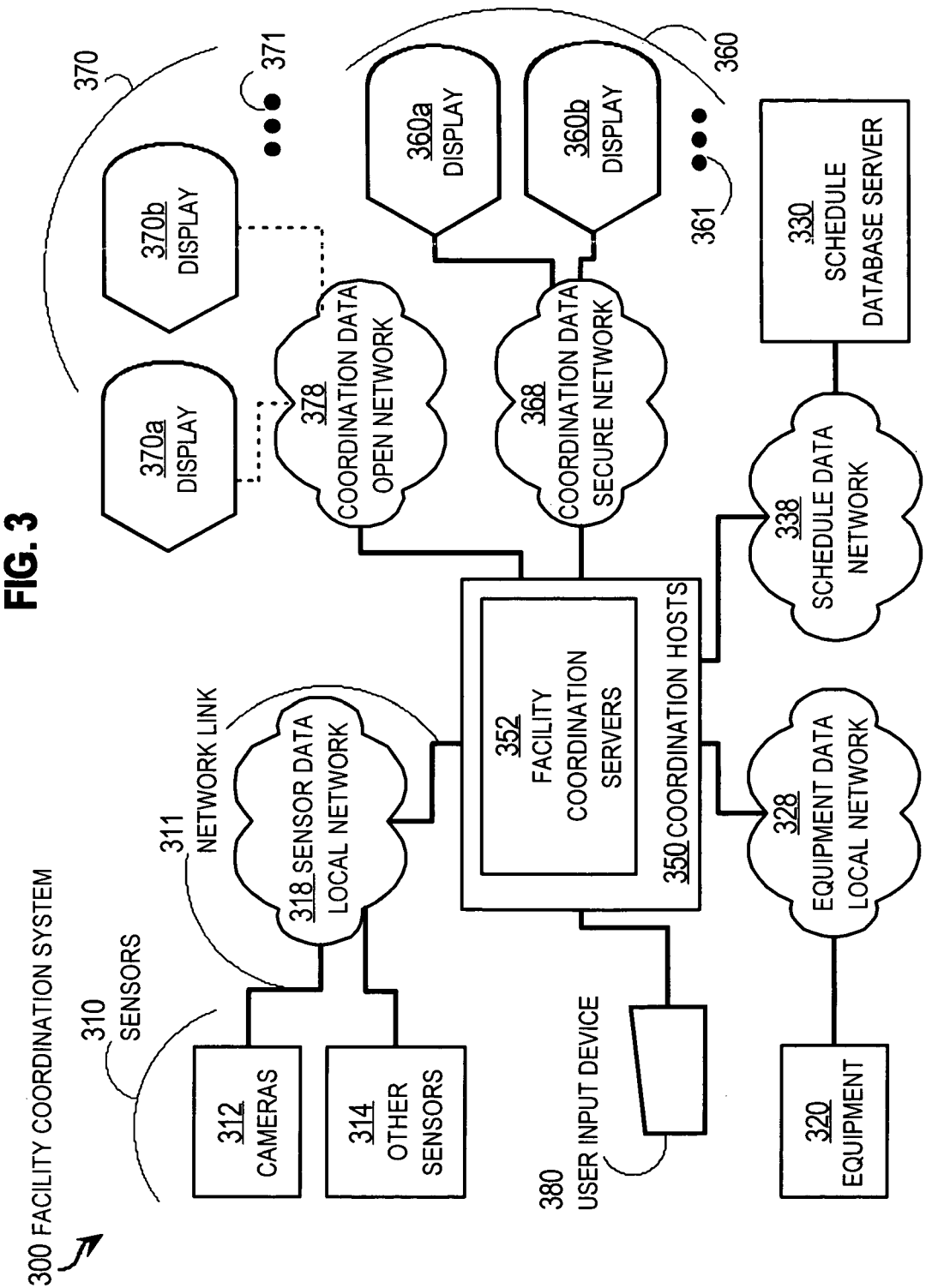
FIG. 3 is a block diagram that illustrates at a high level a facility coordination system, according to an embodiment.

FIG. 3 is a block diagram that illustrates at a high level a facility coordination system 300, according to an embodiment using server processes. The client-server model of computer process interaction is widely known and used. According to the client-server model, a client process sends a message including a request to a server process, and the server process responds by providing a service. The server process may also return a message with a response to the client process. Often the client process and server process execute on different computer devices, called hosts, and communicate via a network using one or more protocols for network communications. The term "server" is conventionally used to refer to the process that provides the service, or the host computer on which the process operates. Similarly, the term "client" is conventionally used to refer to the process that makes the request, or the host computer on which the process operates. As used herein, the terms "client" and "server" refer to the processes, rather than the host computers, unless otherwise clear from the context. In addition, the process executing as a server can be broken up to run as multiple servers on multiple hosts (sometimes called tiers) for reasons that include reliability, scalability, and redundancy, but not limited to those reasons.

The system 300 includes one or more facility coordination servers 352 on one or more coordination host computers 350, and also includes sensors 310, facility equipment 320, networks 318, 328, 338, 368, 378, displays 360, 370, user input device 380 and schedule database server 330. In other embodiments, more or fewer components are included in a facility coordination system.

One or more facility coordination servers 352 are distributed among one or more hosts 350 connected by network elements (not shown). Facility coordination servers 352 perform the steps described above in method 200. Further details for an embodiment of facility coordination servers 352 are described below with reference to FIG. 4.

One or more sensors 310 detect conditions in the facility in support of step 210, described above. Sensors 310 include one or more cameras 312 or one or more other sensors 314 or both, as will be described in greater detail below for some illustrated embodiments.

Sensor data local network 318 provides an electronic communication path from sensors 310 to facility coordination servers 352 using one or more network links 311. Any network and network protocol known may be used. In illustrated embodiments, network 318 is a secure local area network (LAN) that is physically secure from snooping by agents outside the facility to protect sensitive information. In other embodiments, sensor data local network 318 is omitted and sensors 310 communicate directly with facility coordination hosts 350.

Facility equipment 320 includes any equipment used in the facility without regard to the facility coordination servers 352. Some of this equipment communicates over a network. For example, in hospital operating rooms, equipment 320 includes anesthesia equipment, radiological equipment, patient monitoring equipment, and laparoscopy equipment, among others.

Equipment data local network 328 provides an electronic communication path from equipment 320 to data and control servers for that equipment, such as network database servers to store patient data collected by patient monitoring equipment. Any network and network protocol known may be used. In illustrated embodiments, network 328 is a secure local area network (LAN) that is physically secure from snooping by agents outside the facility to protect sensitive information. As illustrated, facility coordination servers 352 are connected to equipment data local network 328 using one or more network links 311 to sniff out network traffic associated with equipment 320. In some embodiments, networks 318 and 328 are the same or share network elements; in some embodiments, networks 318 and 328 are separate and distinct networks. In some embodiments, equipment 320 and network 328 are not included in a facility coordination system.

Displays 360, including displays 360a, 360b and other displays represented by ellipsis 361, and displays 370, including displays 370a, 370b and other displays represented by ellipsis 371, are used to present coordination data as described above in step 270 of method 200. In some embodiments, at least one of displays 360, e.g., display 360a, includes a projector for projecting images onto a whiteboard, such as control desk whiteboard 102 depicted in FIG. 1. The images projected for an illustrated embodiment are described in more detail below with reference to FIG. 5. In other embodiments, more or fewer displays 360, 370 are used.

Coordination data networks, including coordination data secure network 368 and coordination data open network 378 provide electronic communication paths from facility coordination servers 352 to displays 360, 370. Any network and network protocol known may be used. In illustrated embodiments, coordination data secure network 368 is a secure local area network (LAN) that is physically secure from snooping by agents outside the facility to protect sensitive information. Displays 360 are in secure communication with facility coordination servers 352 and can present high detail, highly sensitive coordination information. In some embodiments network 368 is a virtual private network (VPN) on a less secure physical network, including a wide area network (WAN) such as the Internet or a wireless network or both.

Displays 370 are in non-secure communication with facility coordination servers 352, and do not present high detail, highly sensitive coordination information. In some embodiments, coordination data open network 378 is a wireless local network for reaching displays 370 that include hand held devices throughout the hospital, for example to reach physicians on their rounds. In some embodiments, network 378 includes a non-secure wide area network (WAN) such as the Internet or a wireless wide area network to reach displays at remote sites.

In some embodiments, networks 368 and 318 or 328, or some combination, are the same or share network elements; in some embodiments, 368 and 318 and 328 are separate and distinct networks. In some embodiments, displays 370 and network 378 are not included in a facility coordination system.

User input device 380 is any device used to obtain input from any of the persons whose use of the facility is to be coordinated. In some embodiments user input device 380 includes a keypad or keyboard connected to a terminal with one or more of displays 360, 370. In some embodiments user input device 380 includes a card reader, either a stand alone reader or one connected to a terminal with one or more of displays 360, 370. In some embodiments, user input device 380 includes one or more tangible tokens, such a magnetic tokens moved on the whiteboard 102 depicted in FIG. 1. The tangible tokens for an illustrated embodiment are described in more detail below with reference to FIG. 5. Although shown connected directly to coordination hosts 350, in other embodiments, user input device 380 communicates with facility coordination servers 352 indirectly through one or more other networks, such as networks 318, 328, 368, and 378. In some embodiments, user input device 380 is omitted.

Schedule database server 330 is a computer application that provides for scheduling persons or facilities or both; and supports step 202 of method 200, described above. Any system known in the art may be used.

Schedule data network 338 provides an electronic communication path from schedule database server 330 to clients that use the server, such clients on hosts used by hospital administrative staff, charge nurses, surgeons, and maintenance staff. Any network and network protocol known may be used including LANs and WANs. As illustrated, facility coordination servers 352 are connected to schedule data network 338 using one or more network links 311; for example, facility coordination servers 352 include a client for the schedule database server, as described in more detail below. In some embodiments, networks 338 and 318 or 328 or 368 or 378, or some combination, are the same or share network elements; in some embodiments, 338 and 318 and 328 and 368 and 378 are separate and distinct networks. In some embodiments, server 330 and network 338 are not included in a facility coordination system.

3. Detailed Embodiments

Figure 4:
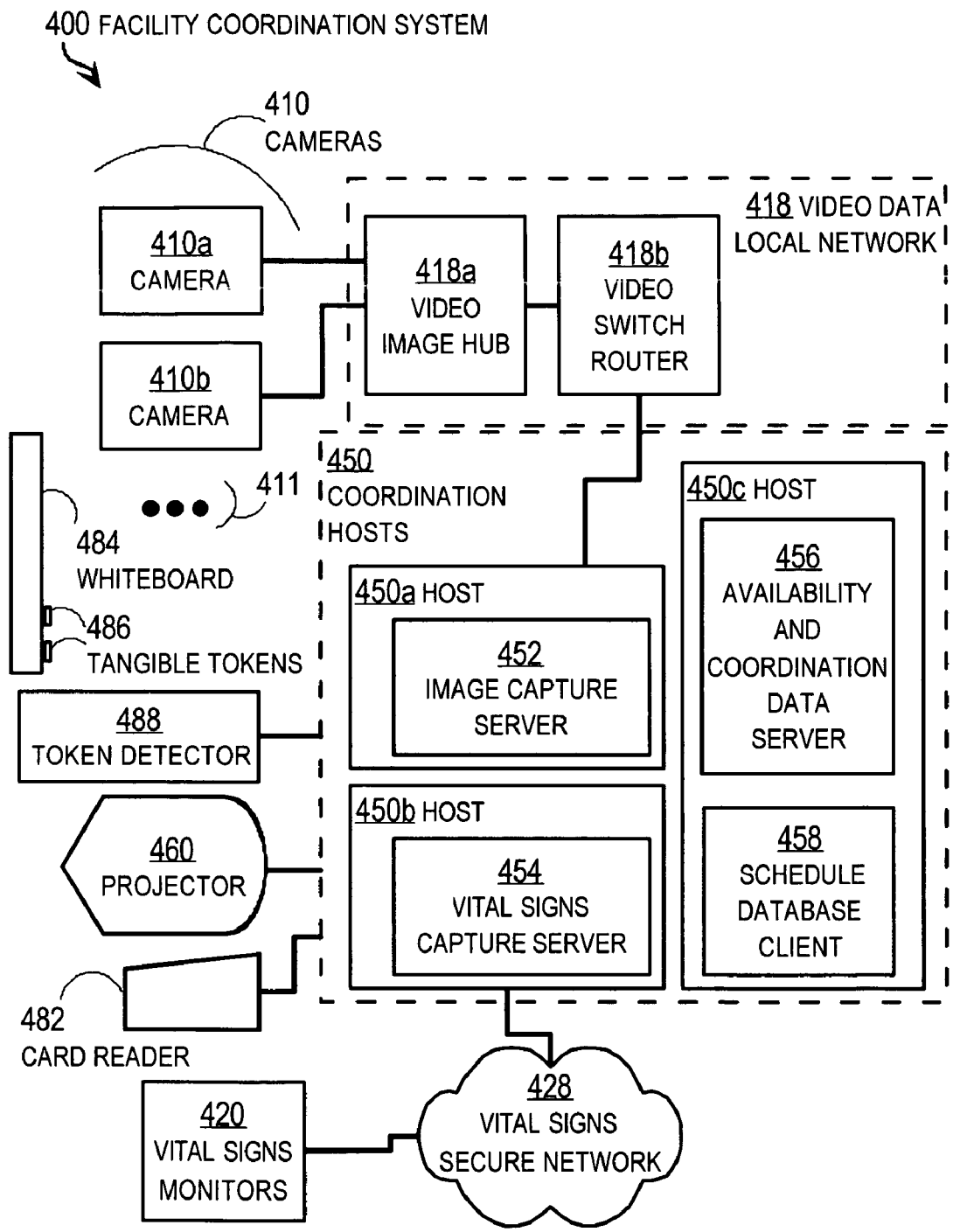
FIG. 4 is a block diagram that illustrates at a more detailed level a facility coordination system, according to another embodiment.

FIG. 4 is a block diagram that illustrates at a more detailed level a facility coordination system 400, according to another embodiment. In the embodiment illustrated in FIG. 4, the sensors 310 of FIG. 3 include cameras 410, including cameras 410a, 410b and other cameras indicated by ellipsis 411. The sensor data local network 318 of FIG. 3 includes a video data local network 418, including video image hub 418a and video switch/router 418b. The equipment 320 of FIG. 3 includes vital signs monitors 420, and the equipment data local network 328 of FIG. 3 includes a vital signs local network 428.

The coordination hosts 350 of FIG. 3 include coordination hosts 450, including hosts 450a, 450b, 450c. The facility coordination servers 352 of FIG. 3 include an image capture server 452 on host 450a, a vital signs capture server 454 on host 450b, and a schedule database client 458 and an availability and coordination data server 456, both on host 450c.

The display 360 of FIG. 3 includes projector 460 and whiteboard 484. The user input device 380 of FIG. 3 includes card reader 482, tangible tokens 486 on whiteboard 484, and token detector 488.

Cameras 410 provide image data for areas both inside and outside the operating room. Any cameras may be used. In some embodiments analog video cameras are used. An American convention for analog video signals, designated NTSC, provide three analog signals representing hue, saturation and brightness values (HSV code) for scanning across a display area of a cathode ray tube. In other geographical regions, a different convention for analog video signals may be used. In some embodiments digital cameras are used, which typically provide three bytes (24 bits) of data representing red, green and blue values (RGB code) for each picture element (pixel) of an image comprising a number N rows and a number M columns. Digital imagery is often stored in as a bitmap of red, green, blue bytes in BMP format. In some embodiments compressed RGB data is produced, using a compression scheme. Any compression scheme may be used; some well known compression schemes include digital formats designated by the names: graphics interchange format (GIF); tagged image file format (TIFF), and joint photographic experts group (JPEG) for individual images and motion picture experts group (MPEG) for video (which is sequences of related images).

In an illustrated embodiment, the cameras 410 include four cameras: one camera in each of three operating rooms and one camera directed to produce images of a whiteboard near the control desk. In other embodiments, cameras 410 include two cameras used in each of six or more operating rooms, so that a view of each room is obtained even when the view of one camera in the room is obstructed by a person or by equipment. In some embodiments, a camera is pointed at each bed location in a holding or staging area, where patients are taken before they are brought into one of the operating rooms.

The video image hub 418a is connected to each camera to receive the video signals as input and allows electronic control of which video signals are output on one or more communication channels. Any known video hub may be used. The video switch/router 418b provides control signals to the video image hub to determine which input signal is to be output for how long and which destination on the network is to receive the video output. Any known network switch or router may be used as video switch/router 418b. The video switch/router 418b is controlled by the image capture server 452 on host 450a, as described in more detail below.

The vital signs monitors 420 include monitors of heart activity (electrocardiogram, EKG), blood oxygen saturation ($SaO_2$), non-invasive blood pressure (NBP), and body temperature (TEMP) in each operating room. Any equipment may be used to measure these vital signs. In an illustrated embodiment, the EKG data, including heart rate (HRATE) data, $SaO_2$ data, NBP data and TEMP data are produced by DASH-Patient Vital Signs Monitor (model Marquette/Solar) of General Electric Corporation's GE Healthcare company of Chalfont St. Giles, United Kingdom. In the illustrated embodiment, the vital signs local network 428 is used to report vital signs data to a central data repository and server (not shown), where the vital signs data can be accessed by certain hospital staff.

The image capture server 452 on host 450a controls video switch/router 418b. The selected video output is transmitted to the image capture server 452. In some embodiments, the image capture server performs pre-processing or image processing on the transmitted video data. Pre-processing includes converting from one coding type to a different coding type, color separation, clipping, filtering, digitizing, decompression or other processing steps. The image capture server 452 communicates with the availability and coordination data server 456 on host 450c to determine what images to capture and what processing to perform and to send the processed results to the availability and coordination data server 456.

In the illustrated embodiment, the vital signs capture server 452 checks ("sniffs") the data packets transmitted on network 428 to detect data packets carrying vital signs data, copies the data and stores the data in a temporary buffer for subsequent analysis, as described in more detail below. In some embodiments, the server 454 performs some or all of the subsequent analysis; in some embodiments, the server 456 performs the subsequent analysis. The vital signs capture server 454 communicates with the availability and coordination data server 456 on host 450c to send the vital signs results to the availability and coordination data server 456.

The schedule database client 458 communicates with the schedule database server 330 to obtain information on the planned used of the facility or personnel or both.

The availability and coordination data server 456 receives the processed image data from the image capture server 452, the processed vital signs data from the vital signs capture server 454 and the schedule data, and determines the availability of the facility. For example, values for parameters that indicate table status and patient status are determined and predictions for the next stage of activity are derived and low detail views of sensitive image data are produced. A subset of the availability data is determined to be coordination data to be presented to the parties that coordinate use of the facility. In the illustrated embodiment, server 456 and client 458 reside together on host 450c. In other embodiments, server 456 resides on a different host than client 458 or server 456 comprises multiple servers which are distributed over several hosts or both.

Whiteboard 484 is any whiteboard that can display a projected image. In an illustrated embodiment, whiteboard 102 is used as whiteboard 484, as described in more detail in the next section with reference to FIG. 5.

Projector 460 is used to project an image that presents coordination data. Any projector may be used. In an illustrated embodiment, projector 460 is a computer display device that projects digital images onto different portions of the whiteboard 484 as described in more detail in the next section with reference to FIG. 5.

Card reader 482 is used to read an identification card belonging to a user of the system in order to determine the identity of a person who can view the coordination data. Any known card reader can be used. In some embodiments card reader uses a magnetic tape on the card; in some embodiments the card reader uses a microchip in the card.

Tangible tokens 486 and token detector 488 are used to indicate user input directly on the magnetic whiteboard. Tangible tokens 486 may include any manually changeable medium that can be detected by a computer. In an illustrated embodiment, described in more detail in the next section with reference to FIG. 5 and FIG. 6A and FIG. 6B, the tangible tokens are visible objects placed on the whiteboard. The tokens may be held on the whiteboard using any method known in the art, such as by magnetic forces or by adhesive, adhesive tape or micro-hooks, such as VELCRO™. Token detector 488 may include any detectors known in the art. In an embodiment described in more detail below, token detector 488 is omitted and a camera 410, e.g., camera 410b, is directed at the whiteboard for collecting an image; and tokens are detected in the image based upon image processing. In some embodiments the image processing to detect tokens is performed in image capture server 452 and in some embodiments the image processing is performed in the availability and coordination data server 456.

3.1 Interface

Figure 5:
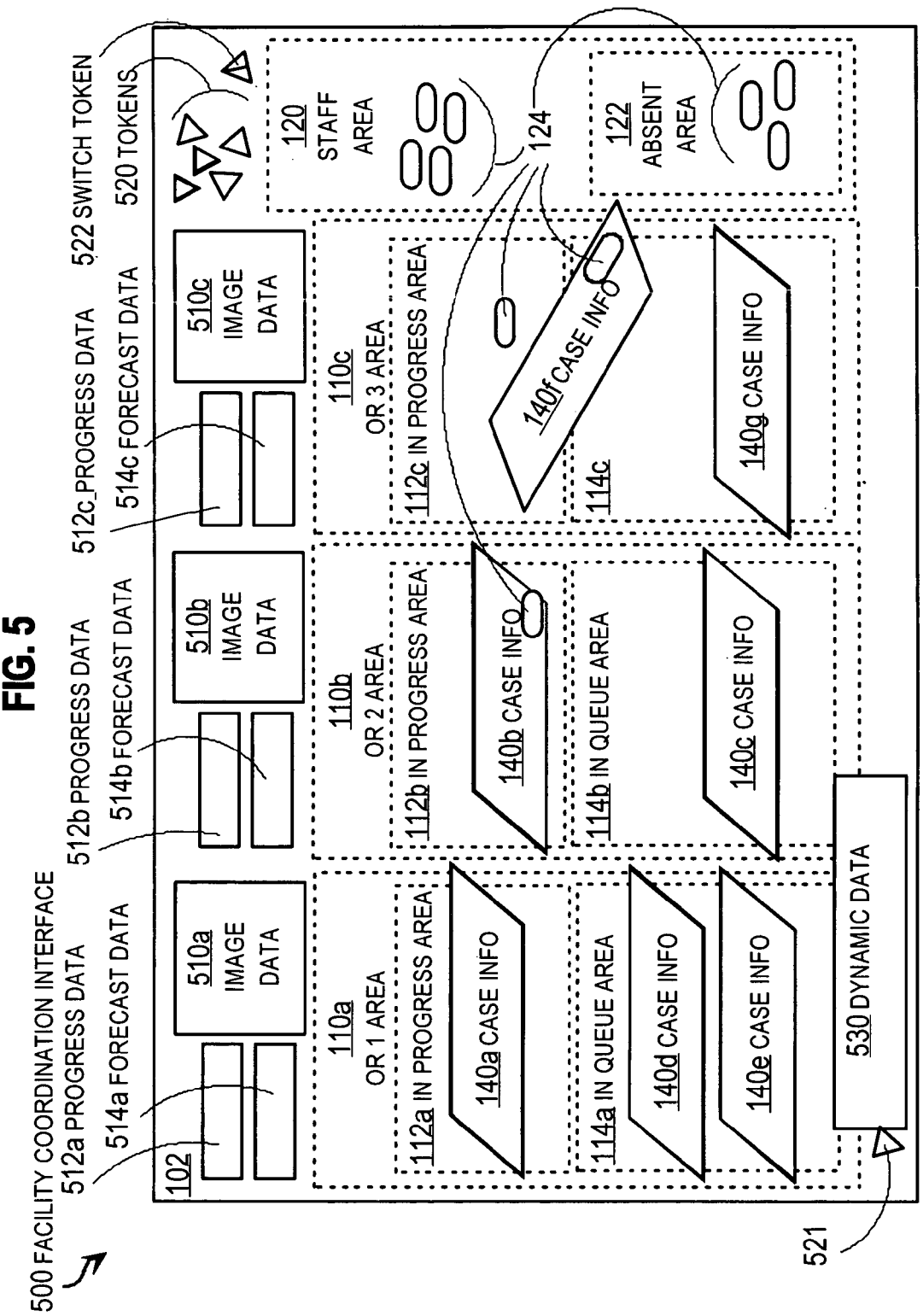
FIG. 5 is a block diagram that illustrates facility coordination system interface, according to an embodiment.

FIG. 5 is a block diagram that illustrates facility coordination system interface 500, according to an embodiment. Interface 500 includes all the elements of coordination system 100 depicted in FIG. 1, including whiteboard 102, case information magnetic strips 140 and magnetic personnel objects 124. In addition, interface 500 includes several presentation items (sometimes called "i-widgets") projected onto whiteboard 102 and also includes tokens 520, 521, 522.

The presentation items projected onto whiteboard 102 include image data 510a, 510b, 510c for operation rooms OR 1, OR 2, OR 3, respectively. The presentation items projected onto whiteboard 102 also include progress data 512a, 512b, 512c for operation rooms OR 1, OR 2, OR 3, respectively. The presentation items projected onto whiteboard 102 also include forecast data 514a, 514b, 514c for operation rooms OR 1, OR 2, OR 3, respectively. In addition, the presentation items projected onto whiteboard 102 also include other dynamic data 530. Although progress data and forecast data and other dynamic data are shown as non-overlapping areas in FIG. 5 for purposes of illustration, in other embodiments, progress data or forecast or other dynamic data, or some combination, are presented in the same or overlapping areas.

Any method may be used to project presentation items onto whiteboard 102. In an illustrated embodiment, the projector 460 can cover a large portion of whiteboard 120 with a large number of rows and columns of pixels. A subset of these rows and columns of pixels are dedicated to each presentation item (i-widget). For example, the projector covers most of the whiteboard 102 with 2400 rows and 3200 columns, and reserves one subset of 300 rows and 400 columns for image data 510a, one subset of 100 rows and 400 columns for progress data 512a, and another subset of 100 rows and 400 columns for forecast data 514a.

Each image data for an operating room, e.g., image data 510a for OR 1, includes coordination data based on conditions data collected from a camera for OR 1, including a camera directed onto a staging area or holding area for OR 1. The detail apparent in image data 510a depends upon the privilege level of a person viewing the interface 500. For example, the image data 510a depicts a low resolution or cartoon image derived from one camera in OR 1. If a doctor presents identification to the system, such as by swiping an ID card in card reader 482, a higher resolution image is shown in image data 510a. In one embodiment, a non-cartoon image is presented in image data 510a. In another embodiment, the size of image data 510a is increased, for example to 600 rows and 800 columns of pixels, so that four times the detail is presented in image data 510a. In some embodiments, one or more other presentation items are turned off in order to make room for the larger image data with more detail.

The progress data for each operating room, e.g., progress data 512a for OR 1, includes progress data included in availability data determined by the facility coordination system. In an illustrated embodiment, facility coordination system 400 presents information in progress data 512a that indicates the current state of the use of the OR. For example, progress data 512a indicates that OR 1 is empty, or is ready for the next patient, or is occupied, or that a procedure is underway that started forty minutes earlier. In some embodiments, progress data 512a also includes a statement of accuracy for the data. For example, progress data 514a includes data that indicates a probability that the status is incorrectly deduced from the image data, e.g., the progress data indicates that the table status is "empty" and that there is a probability of 10% that the status value is not correct. Any method may be used to present this information.

The forecast data for each operating room, e.g., forecast data 514a for OR 1, includes forecast data included in availability data determined by the facility coordination system. In an illustrated embodiment, facility coordination system 400 presents information in forecast data 514a that indicates a future time for a subsequent stage of use of the OR. For example, progress data 512a indicates that OR 1 is occupied but forecast data 514a indicates that OR will be ready for the next patient at a particular time 1 hour and 35 minutes in the future. For purposes of illustration, it is assumed that this forecast is based on the start time for the current procedure and a typical duration for such procedures, and typical delays to remove the patient and ready the table for the next patient. Any method may be used to determine and present this information. In some embodiments, forecast data 514a also includes a statement of accuracy for the forecast. For example, forecast data 514a includes a time error associated with two standard deviations about the forecast time based on a Gaussian or Poisson error distribution around the predicted time. Any method may be used to determine and present this information.

Other dynamic data is presented in dynamic data 530. For example date and time for the current moment is included in dynamic data 530, or a low-resolution image of the corridor or a general holding area is included in dynamic data 530.

In some embodiments, the location of presentation items 510a, 510b, 510c, 512a, 512b, 512c, 514a, 514b, 514c, 530 can be moved around whiteboard 102 from default or predetermined positions using tokens 520. For example, to move image data 510b from the predetermined position, as shown, to a position in the in queue area 114b, a token 520 is moved to the in queue area 114b. In some embodiment, the tokens 520 have unique markings and a token with markings designating image data for OR 1, or image data for a staging room for OR 1 is moved to in queue area 114b. In some embodiments, the tokens are not distinguished from each other. In some such embodiments, a token 520 is first moved to image data 510b to associate the token with the image, and then the token is moved to in queue area 114b to drag the image data 510b with the newly associated token. In the illustrated embodiment, token 521 has been used to position the dynamic data 530 at the bottom of whiteboard 102. Tokens not currently used to provide input or position presentation items are parked in a particular area of the whiteboard, for example the upper right of whiteboard 102, as shown in FIG. 5.

In some embodiments, switch tokens that indicate more than two states are used to provide input on the interface 500 to a facility coordination system. For example, token 522 is a switch token that indicates any one of several states based on a direction of a line bisecting one angle of the triangular shaped token. The bisected angle indicates a direction, e.g., upper left as depicted in FIG. 5. By pointing the bisected angle in different directions, different states can be indicated. This switch token may be used in any way on the interface 500. For example, in some embodiments, the switch 522 token is used with each of image data 510a, 510b, 510c, to switch between a first camera in an operating room, to a second camera, to a third camera in a staging area for the operating room, to a recovery room for a patient currently in the operating room by pointing the bisected angle left, right, up and down, respectively.

Figure 6A:
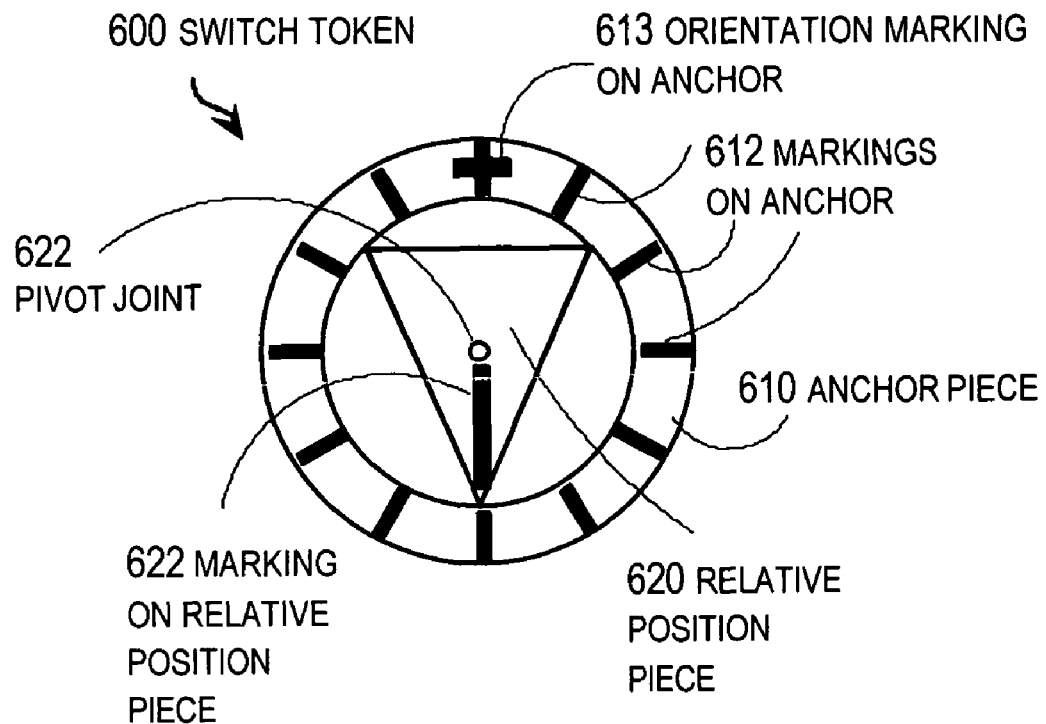
FIG. 6A and FIG. 6B are block diagrams that illustrate switch tokens for a user interface, according to embodiments.
Figure 6B:
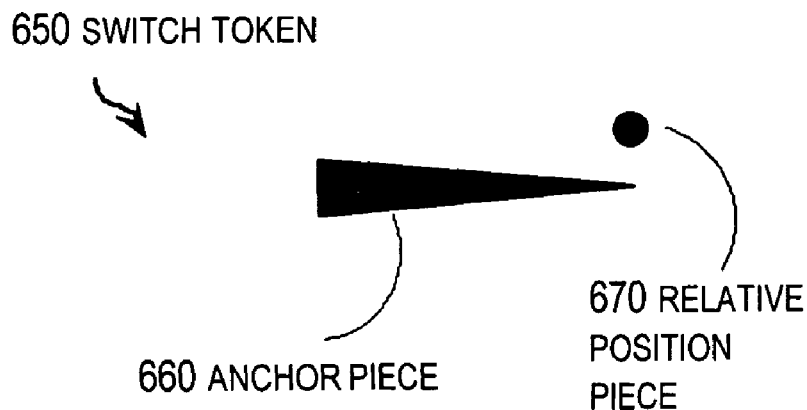

FIG. 6A and FIG. 6B are block diagrams that illustrate switch tokens 600, 650, respectively, for a user interface, according to other embodiments. Switch token 600, depicted in FIG. 6A includes a circular anchor piece 610 and a relative position piece 620 moveably mounted to the anchor piece at a pivot joint 622. One or more markings 612, 613 on anchor piece 610 and one or more markings 622 on relative position piece are used by image processing techniques to determine which state of multiple states the switch is in. Any image processing techniques may be used. The illustrated switch token 600 easily distinguishes among 12 states for the relative position piece. The orientation marking 613 removes ambiguity about the twelve states due to symmetry of the anchor piece.

Switch token 650, depicted in FIG. 6B, includes a triangular anchor piece 660 and a circular relative position piece 670 independently moveable from the anchor piece. The two dimensional distances from the relative position piece 670 to the short base of the triangular anchor piece 660 (distances perpendicular and parallel to the axis of symmetry of the anchor piece) are used by image processing techniques to determine which state of multiple states the switch is in. Any image processing techniques may be used.

3.2 Image Data

The coordination image data 510*a*, 510*b*, 510*c* on the interface 500 is derived from image data on the conditions of the facility measured by cameras 410. FIG. 7A is a flow diagram that illustrates a facility coordination method 700 using sensitive image data, according to an embodiment. Method 700 is an embodiment of method 200 in which step 210 includes step 710, step 230 includes step 730, step 250 includes step 750, and step 270 includes step 770.

Figure 7B:
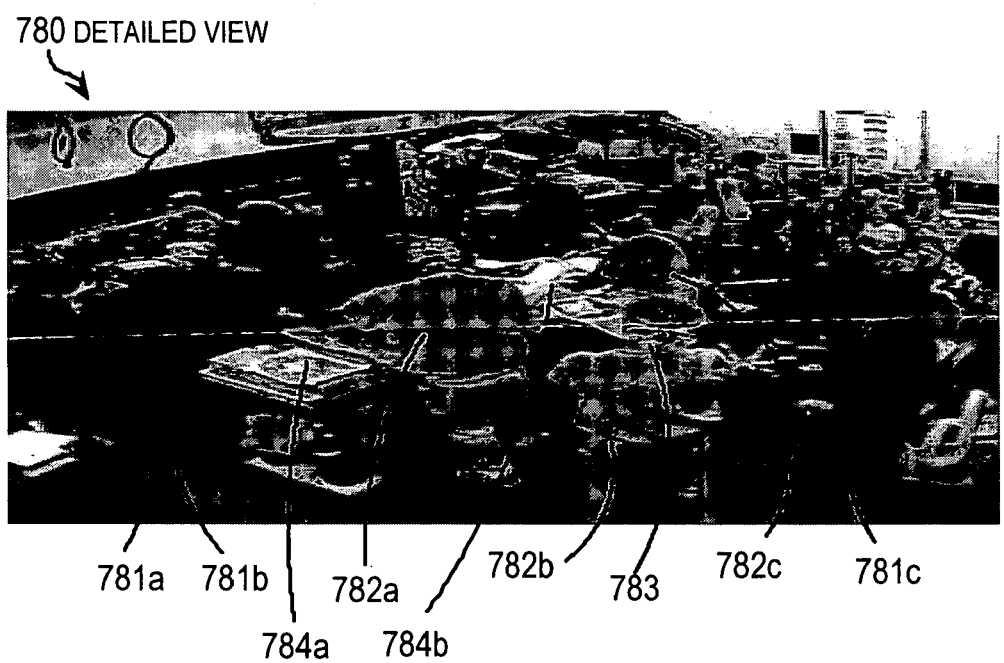
FIG. 7B is an image that illustrates a sensitive detailed view of an operating room, according to an embodiment.

In step 710, raw image data for an operating room is captured. Any method may be used to capture the raw image data. An example of a raw image of an operating room is depicted in FIG. 7B. FIG. 7B is a black and white version of a color image that illustrates a sensitive, detailed view 780 of an operating room, according to an embodiment. As can be seen in FIG. 7B, the operating room includes supplies along the visible walls, an operating table in the middle of the room, and equipment. Also visible in this view are persons acting within the operating room during a process to clean the room. These persons are dressed in operating room garb called "scrubs." Three persons are dressed in green scrubs 781*a*, 781*b*, 781*c*. Three persons are dressed in pink scrubs 782*a*, 782*b*, 782*c*. All persons are wearing hairnets, including a blue hairnet 783 worn by person wearing pink scrubs 782*b*. The operating table is partly covered in white cloths 784*a*, 784*b*. The detail visible in view 780 exceeds what is needed to determine that the room is being cleaned, and is considered an invasion of the privacy due the personnel involved.

Figure 7C:
FIG. 7C is an image that illustrates a less sensitive, cartoon view of an operating room, according to an embodiment.

In step 730 a cartoon image view 790 is derived based on the raw detailed view 780. FIG. 7C is a black and white version of a color image that illustrates a less sensitive, cartoon view 790 of the operating room, according to an embodiment. In the cartoon view 790 certain objects visible in the detailed view 780 and considered sensitive for reasons of privacy are represented by solid colored shapes. The three persons dressed in green scrubs 781*a*, 781*b*, 781*c* are represented as solid green shapes 791*a*, 791*b*, 791*c*, respectively. The three persons dressed in pink scrubs 782*a*, 782*b*, 782*c* are represented as solid pink shapes 792*a*, 792*b*, 792*c*, respectively. The blue hair net 783 is represented as solid violet shape 793. The white cloths 784*a*, 784*b* are apparent as solid white shapes 794*a*, 794*b*, respectively. No other shapes are included in this cartoon image. Lighting and shading and nuances of color changes that indicate details of a person's weight and conditioning and other distinctive features are eliminated in the cartoon image. Faces are excluded. The invasion of privacy is significantly reduced. Step 730 includes steps 732, 734, 746, 738.

In step 732, the raw image is low passed filtered to eliminate fine grained details on the order of about ten pixels and less.

In step 734, the RGB coded pixels are converted to HSV coded pixels. HSV code is convenient for the purpose of cartooning because a single color with varying shades of brightness has a relatively constant hue value and saturation value, e.g., all of the green scrubs have nearly the same hue and saturation values, with the shading of folds indicated by relatively large swings in brightness values. In some embodiments step 734 is omitted. For example, in some embodiments, cartooning is done on RGB coded pixels. In some embodiments, the raw image data is received in HSV coded analog or digital (pixel) signals. In some embodiments, step 730 includes digitizing analog HSV values to HSV coded pixels. In some embodiments, step 730 includes digitizing analog HSV values to RGB coded pixels.

In step 736, ranges of coded values that represent sensitive objects are mapped to a single color for the solid filled shapes. For example, in some embodiments, ranges of hue values and saturation values associated with pink scrubs are mapped to a single pink color defined by a particular red value a particular green value and a particular blue value (a particular RGB set of values). Similarly, ranges of hue and saturation values associated with various other sensitive objects (such as green scrubs, blue hair nets and white table cloths) are mapped to corresponding single colors (such as green, violet and white).

In some embodiments using RGB codes, ranges of red, green and blue values in pixels associated with pink scrubs are mapped to a single pink color defined by a particular red value a particular green value and a particular blue value. Similarly, ranges of red, green and blue values in pixels associated with various other sensitive objects (such as green scrubs, blue hair nets and white table cloths) are mapped to corresponding single colors (such as green, violet and white). In some embodiments this mapping is retrieved from computer storage based on ranges and solid colors predetermined by analysts examining sample images. In some embodiments this mapping is retrieved from computer storage based on ranges and solid colors predetermined by image processing of sample images. In some embodiments this mapping is performed dynamically and adaptively by image processing of recent past images.

In step 738, a cartoon view image is generated by combining the solid color objects onto a base image. In the illustrated embodiment depicted in FIG. 7C, the base image is a blank (black) image. In some embodiments, the base image is the original high detailed image, so that the sensitive objects are replaced by cartoons while other less sensitive objects are left substantially unchanged to provide more context for the cartoon view.

In the illustrated embodiment, the single cartoon image depicted in black and white in FIG. 7C is difficult to interpret without FIG. 7B for reference. In practice, a sequence of cartoon views derived from a sequence of images in a video clip provide a moving carton that is more easily interpreted to represent humans moving about an operating table in an operating room.

In step 750, it is determined that the persons with access to the interface 500 have low privileges to view the operating room details. For example, it has been more than five minutes since a doctor or nurse with a high privilege has swiped an ID card in card reader 482.

In step 770 the cartoon view image is presented to the parties coordinating the use of the operating rooms. For example, the system 400 does not display the full detail image as image data 510*a*, 510*b*, or 510*c* of the interface 500, but instead displays cartoon views as image data 510*a*, 510*b*, or 510*c* of the interface 500.

3.3 Equipment Data

Figure 8A:
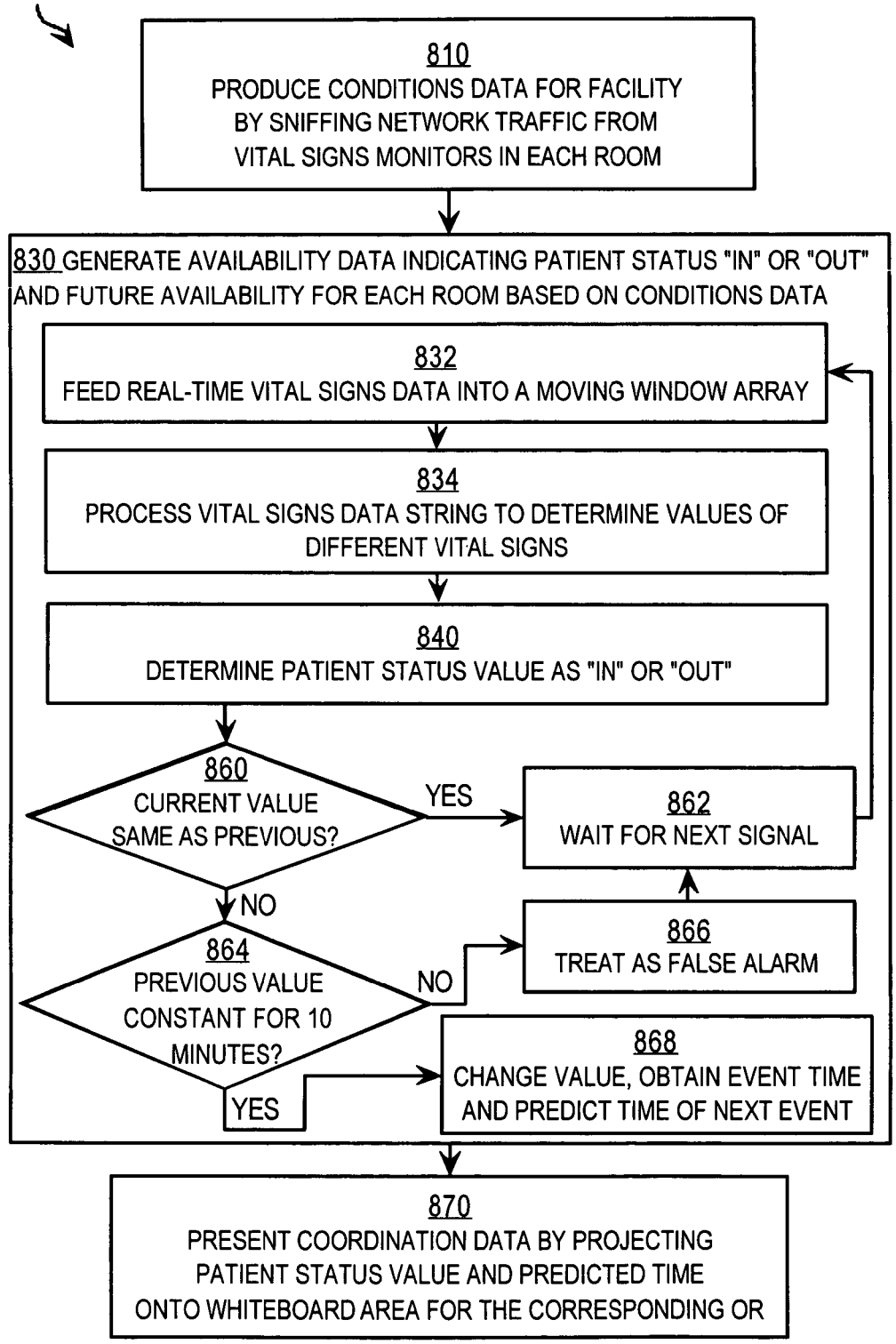
FIG. 8A is a flow diagram that illustrates a facility coordination method using vital signs monitoring data, according to an embodiment.

FIG. 8A is a flow diagram that illustrates a facility coordination method 800 using vital signs monitoring data, according to an embodiment. Method 800 is an embodiment of method 200 in which step 210 includes step 810, step 230 includes step 830, and step 270 includes step 870.

In step 810, facility conditions data is produced by sniffing network traffic from vital signs monitors in each room. In an illustrated embodiment, a hospital where the operating rooms are located uses General Electric (GE) vital signs monitors that report their output over a hospital real-time GE vital signs internal network (intranet). The vital signs information in data packets transmitted over this intranet are gathered and translated into records of vital signs for each operating room. Sniffing network traffic is an advantage because step 810 does not interfere with or require any changes to the operation or communications with the equipment, e.g., does not modify communications of the GE vital signs monitors and GE data reporting network. In the illustrated embodiment, none of the patient identification information is used or displayed, except for a patient or case number.

In step 830, availability data indicating patient status "in" or "out" is generated along with future availability for at least one operating room. In some embodiments, a vital-signs status of "on" or "off" corresponding to a patient status "in" or "out," respectively, is used. In some embodiments, the future availability is omitted. For example a patient status parameter is filled with a value indicating "in" or a value indicating "out," e.g., variable patientStatus=1 for "in" and patientStatus=0 for "out." Step 830 includes steps 832, 834, 840, 860, 862, 864, 866, 868.

In step 832, real time vital signs data collected from the network is fed into an array that represents a moving temporal window. Any method may be used to fill the array with the vital signs data.

In step 834, text strings in the vital signs data are used to determine values of a set of vital signs parameters, called a record of vital signs, including values for the parameters representing heart rate (HRATE) derived by the monitor from data along five leads from the electrocardiograph, blood oxygen saturation (O2SAT), non-invasive blood pressure (NBP) and body temperature (TEMP). Multiple records of values for these parameters are included in the moving temporal window. For example, for purposes of illustration it is assumed that the moving temporal window is five minutes long and a record is obtained every 10 seconds, so there are 30 records included in the moving window array.

Figure 8B:
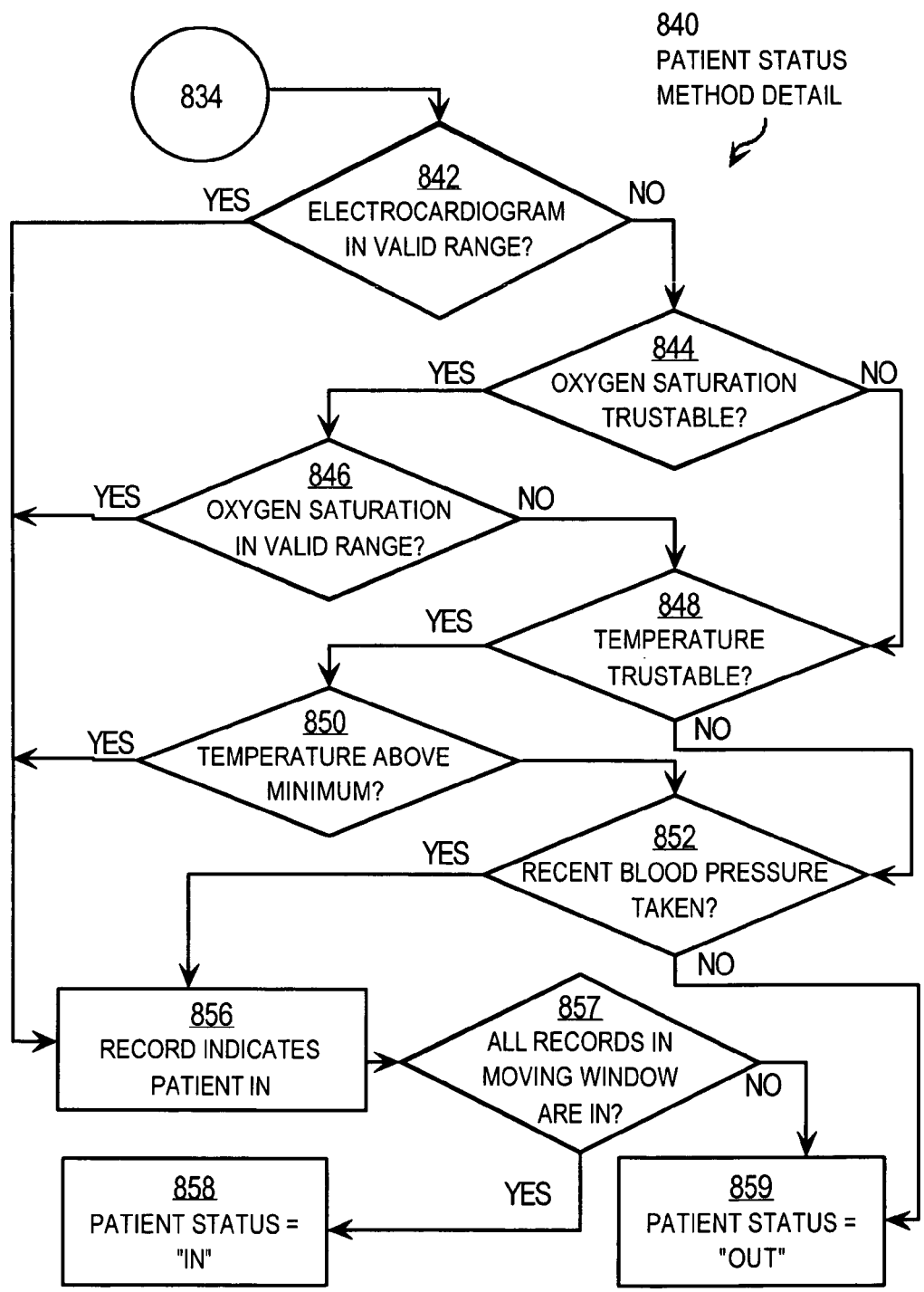
FIG. 8B is a flow diagram that illustrates a method detail of the facility coordination method of FIG. 8A, according to an embodiment.

In step 840, a tentative patient status is determined based on the data in the moving window array. FIG. 8B is a flow diagram that illustrates a method detail for step 840 of the facility coordination method of FIG. 8A, according to an embodiment. Control passes to step 842 from step 834.

In step 842, it is determined whether the electrocardiogram data for the current record is in a valid range. For example, it is determined that the heart rate HRATE value is greater than a minimum heart rate of a living person and less than maximum heart rate of a living person.

If it is determined that the electrocardiogram data is in a valid range, then it is determined that the current record indicates that a patient is "in" and control passes to step 856. If it is determined that the electrocardiogram data is not in a valid range, then control passes to step 844 to check data from the other monitors to determine whether the patient is "in." This is done because the patient might not yet be hooked to the electrocardiograph, or the electrocardiograph might be malfunctioning.

In step 844 it is determined whether data for the oxygen saturation monitor can be trusted. If not, the determination of patient status will be based on one of the other monitors. For example, in the GE vital signs data reporting system, when the oxygen saturation sensor is producing suspicious or sporadic readings, the TEMP value is reported before the O2SAT value. Some suspicious readings may be in a valid range for blood oxygen saturation levels in a living patient. In some embodiments, therefore, the oxygen saturation sensor is not considered trustable if the TEMP value precedes the O2SAT value in the data record. The O2SAT value is also not trusted if the status based on the O2SAT values disagrees with the previous status. This decision is made because the status should change once and remain in the same state for an extended period involving many records (on the order of tens of minutes). If it is determined in step 844 that the O2SAT value is trustable, then control passes to step 846 to determine whether the value is in range for a living patient.

In step 846, it is determined whether the O2SAT value is in range for a living patient, e.g, it is determined whether the O2SAT value is within the range from about 50% to 100% saturation. If so, then it is determined that the current record indicates that a patient is "in" and control passes to step 856. If the O2SAT value is outside this range, or if it is determined in step 844 that the O2SAT value is not trustable, control passes to step 848 to check the TEMP value.

In step 848, it is determined whether the temperature sensor is trustable. The TEMP value is also not trusted if the status based on the TEMP values disagrees with the previous status. If it is determined in step 848 that the TEMP value is trustable, then control passes to step 850 to determine whether the value is in range for a living patient.

In step 850, it is determined whether the TEMP value is in range for a living patient, e.g., it is determined whether the TEMP value is above some minimum temperature. In some embodiments, the GE vital signs monitors provide two body temperature sensors, TEMP1 and TEMP2. In these embodiments it is determined whether either the TEMP1 or TEMP2 value is above some minimum temperature. In some embodiments, the minimum temperature for passing TEMP1 is different from the minimum temperature for passing TEMP2. If either temperature value is above the appropriate minimum, then it is determined that the current record indicates that a patient is "in" and control passes to step 856. If the TEMP value is below the appropriate minimum, or if it is determined in step 848 that the TEMP value is not trustable, control passes to step 852 to check the NBP data.

In step 852 it is determined whether a non-invasive blood pressure (NBP) measurement is recent, i.e., was taken within a specified time before the present time. Operating room protocol calls for taking the patient's blood pressure periodically (e.g., on the order of every 10 minutes). Therefore, in this example, if no blood pressure has been taken in the last 10 minutes, then it is determined that a patient is not "in." If a blood pressure measurement has been taken within the specified time, then it is determined that the current record indicates that patient is "in" and control passes to step 856.

In step 856, the patient status for the record is set to "in" and control passes to step 857. In step 857, it is determined whether all the records in the moving temporal window have a patient status of "in." If so control passes to step 858.

In step 858, a variable is set to indicate a tentative patient status equal to "in" for the moving window and control passes to the step 860 in method 800 of FIG. 8A.

If it is determined in step 852 that no NBP measurement is within the specified time, or if it is determined in step 857 that not all the records in the moving temporal window have a patient status of "in," then control passes to step 859. In step 859, a variable is set to indicate a tentative patient status equal to "out" for the moving window and control passes to the step 860 in method 800 of FIG. 8A.

In step 860, it is determined whether the value of the variable for the moving temporal window is the same as the previous value stored in the parameter variable patientStatus. If so, there is no change to the status and control passes to step 862.

In step 862, the server waits for the next signal from the vital signs monitor. Control passes back to step 832 to feed the new signal into the moving window.

If it is determined in step 860 that the value of the variable for the moving temporal window is not the same as the previous value stored in the parameter variable patientStatus, control passes to step 864 to respond to the change.

In step 864, it is determined whether the previous value was constant for a specified period of time, e.g., ten minutes. In this embodiment, not only is the value of the status stored in the variable patientStatus, but also a start time for the status is stored, e.g., in a variable called patientStatusEventTime. If the previous value was not constant for the specified period, e.g., if the patientStatusEventTime is more recent than the specified period of time before the present time, then control passes to step 866. In step 866, the change is considered a false alarm because patient status should remain constant for at least the specified period of time. Control then passes to step 862 to wait for the next signal from the vital signs monitoring equipment.

If it is determined in step 864 that the previous value was constant for the specified period of time, then control passes to step 868. In step 868 the value for the parameter varaible patientStatus is changed to the newly determined status and the parameter variable patientStatusEventTime is set to the present time.

In the illustrated embodiment, a predicted time for the next event is also determined during step 868. For example, based on a change to patient status "out," and statistics for past delays from one patient "out" to operating table "ready" a prediction is made of the future time the operating table will be ready. In some embodiments a predicted time is not determined.

In step 870, the patient status value is projected onto the whiteboard 102 in progress data, e.g., in progress data 512a for OR 1. In some embodiments, step 870 includes projecting the predicted time for the operating table ready onto the whiteboard 102 in forecast data, e.g., forecast data 514a for OR 1.

FIG. 9 is a flow diagram that illustrates a facility coordination method 900 using non-intrusively measured equipment operation data, according to an embodiment. Method 900 is an embodiment of method 200 in which step 210 includes step 910, step 230 includes step 930, and step 270 includes step 970.

In step 910, facility conditions data is produced non-intrusively by detecting electromagnetic or vibration emissions from equipment in the operating room. This is accomplished using an emission detector as a sensor 310 in system 300 depicted in FIG. 3. In an illustrated embodiment, a hospital uses a Bovie knife that cuts tissue and simultaneously cauterizes blood vessels using electricity. The available Bovie knife models each emit electromagnetic waves with a peak amplitude somewhere in the frequency range from about 350 to about 800 kiloHertz (kHz, 1 kHz=$10^3$ cycles per second) when operated to cut tissue. In step 910, the electromagnetic emission in this frequency band are detected and recorded. Any method may be used to detect and record the emissions, including using amplitude modulation (AM) radio tuners and tape recorders for emission in the range from 540 to 800 kHz. In some embodiments, step 910 includes signal processing (such as filtering) and digitization to produce a digital signal. The detecting and recording of electromagnetic emission is an advantage because step 910 does not interfere with or require any changes to the operation of the Bovie knife models.

In step 930, availability data indicating incision status as "pre-incision" or "post-incision" is generated along with future availability for at least one operating room. In some embodiments, the future availability is omitted. For example, a patient status parameter is filled with a value indicating "pre-incision" or a value indicating "post-incision," e.g., variable incisionStatus=0 for "pre-incision" and incisionStatus=1 for "post-incision." Step 930 includes steps 932, 934, 960 and 968.

In step 932, the variable incisionStatus for the incision status parameter is set to a pre-incision value when the value of the patient status parameter, as indicated by the variable patientnStatus described above, changes from "out" to "in." This initializes the parameter.

In step 934, a real-time digital signal from the electromagnetic emissions is fed into a temporal window array.

In step 960 it is determined whether the spectral signature of a Bovie knife operation is reliably detected in the temporal window. For example, in an illustrated embodiment, a Bovie knife operation is detected if a spectral peak exceeding certain impedance is found centered on an appropriate frequency. The frequency of the peak, the width of the peak and the peak level above background noise are easily determined through routine experimentation. In an illustrated embodiment, the Bovie unit works in a pre specified radio frequency. By focusing on the known frequency range the effects of noise are reduced or eliminated and a distinguishable and reliable signature is produced. In some embodiments, knife operation signatures must persist for a specified period of time, such as one minute, to qualify as a reliable detection.

If it is determined in step 960 that the signature of Bovie knife operation is not detected, control passes back to step 934 to feed the next real-time signals into the moving temporal window array. If it is determined in step 960 that the signature of Bovie knife operation is detected, control passes to step 968.

In step 968, the value for the parameter variable incisiontStatus is changed to a value indicating "post-incision" and the parameter variable incisionStatusEventTime is set to the present time.

In the illustrated embodiment, one or more predicted times for subsequent events are also determined during step 968. For example, based on a change to incision status "post-incision," and statistics for durations of past procedures of similar kind, a prediction is made of the future time when the procedure will be finished. Based on this prediction other stages can also be predicted. For example, a time can be predicted when the patient will be ready to be removed from the operating room, and a tiem can be predicted when the table is empty or ready for the next patient. In some embodiments a predicted time is not determined.

In step 970, the incision status value or the predicted time is projected onto the whiteboard 102 or both. For example, in an illustrated embodiment the incision status value is projected onto whiteboard 102 in progress data, e.g., in progress data 512a for OR 1. In the illustrated embodiment, step 970 includes projecting the predicted time for the completion of the current procedure, for the drapes off stage, for the table empty stage, or for the table ready stage, or some combination, onto the whiteboard 102 in forecast data, e.g., in forecast data 514a for OR 1.

3.4 Plan Deviation Display

The progress data displayed, for example the progress data 512a for OR 1 projected onto whiteboard 102, may be presented in any form. Progress is often reported with a progress bar, in which a variable length bar represents progress between 0% and 100%. However, such a progress bar fails to indicate to users of a facility how far actual uses are deviating from planned uses. What is needed is a way to display plan deviations in the progress data.

Figure 10A:
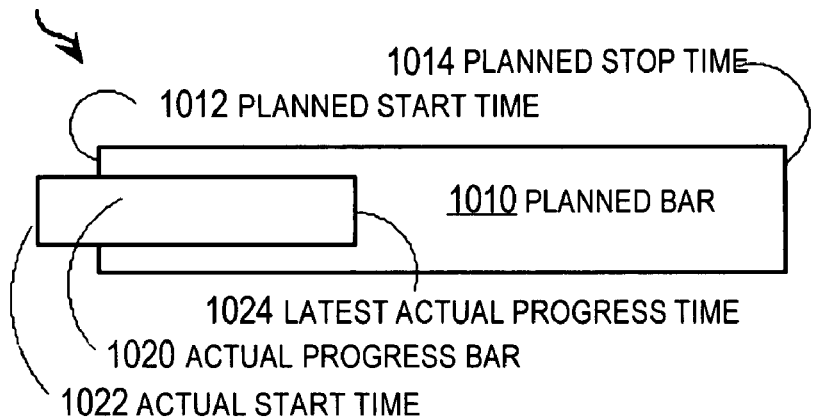
FIG. 10A, FIG. 10B and FIG. 10c are block diagrams that illustrate plan deviation displays, according to some embodiments.
Figure 10B:
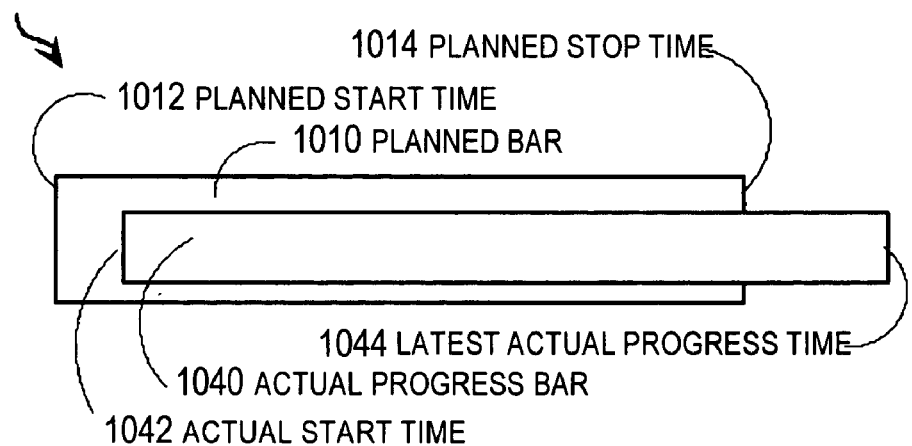
Figure 10C:
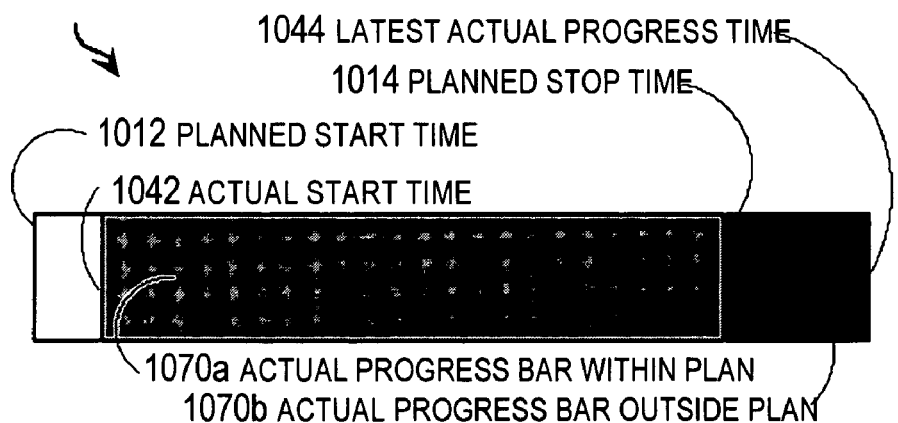

FIG. 10A, FIG. 10B and FIG. 10c are a block diagrams that illustrate plan deviation displays, according to some embodiments. In FIG. 10A, a deviation display 1000 includes a planned bar 1010 and an actual progress bar 1020. The planned bar extends from a planned start time 1012 for use of the facility to a planned stop time 1014 for use of the facility on a time line (not shown). The length of planned progress bar indicates the expected duration of the procedure. Deviation from the planned use is displayed by an actual progress bar with a start time 1022 that does not align with the planned start time 1012. The actual progress bar ends at the latest actual progress time 1024, which is the current time for a procedure still underway in the facility and is the actual stop time for procedure that has finished.

In FIG. 10B, a deviation display 1030 includes the planned bar 1010 from FIG. 10A and an actual progress bar 1040. The actual progress bar 1040 begins at an actual start time 1042 and ends at the latest actual progress time 1044, which is the current time for a procedure still underway in the facility and is the actual stop time for procedure that has finished. Deviation from the planned use is displayed by an actual progress bar with a start time 1042 that does not align with the planned start time 1012 and a latest actual progress time 1044 that does not align with the planned stop time 1014.

Unlike usual progress bars in which progress is indicated by a bar that begins at 0% and ends at or before 100%, the deviation displays 1000, 1030 include an actual progress bar 1020, 1040 that extends beyond the limits of a second bar indicating the planned use.

In deviation displays 1000, 1030, the actual progress bars 1020, 1040 are narrower than the planned progress bar 1010. In other embodiments, the actual progress bars 1020, 1040 are wider than the planned progress bar.

In FIG. 10C, a deviation display 1060 includes the planned bar 1010 and an actual progress bar 1070 that are the same width. For comparison purposes, planned bar 1010 and the actual progress bar 1070 have the same start and stop times as planned bar 1010 and actual progress bar 1040, respectively, depicted in FIG. 10B. The actual progress bar 1070 begins at the actual start time 1042 and ends at the latest actual progress time 1044, which is the current time for a procedure still underway in the facility and is the actual stop time for procedure that has finished.

Deviation is indicated by color or shading differences for different sections of the overlapping bars. Where the planned bar 1010 does not overlap the actual progress bar 1070 the display has one color or shading type. Where the planned bar 1010 and the actual progress bar 1070 overlap in section 1070a, the actual progress is within the plan and the display has a second color or shading type. Where the actual bar 1070 does not overlap the planned progress bar 1010 in section 1070b, the actual progress extends outside the plan and the display has a third color or shading type. In some embodiments, different colors or shading is used for actual progress that occurs before the planned start time than is used for actual progress that extends after the planned stop time. For example, in an embodiment, a green color is used to indicate an early start and a red color is used to indicate a late finish.

In any of the deviation displays 1000, 1030, 1060, the length of the planned bar may be fixed and the actual progress may extend as far outside the planned bar 1010 as needed to indicate actual progress. In some embodiments, the extent outside the planned bar is presented on logarithmic or other non-linear scale to prevent the display from becoming too big.

In some embodiments, the actual progress bar is allowed to extend only to a predefined maximum length. For example, the maximum length is matched to fit within a progress data area 512 of a projection on a whiteboard. In such embodiments, as the actual progress continues in time, the planned bar is reduced in length proportionately to demonstrate the difference between the actual and planned use. As described above, in some embodiments the either or both bars, of portions of bars, in the display are plotted on a logarithmic or non-linear scale.

4. Computer Hardware Overview

Figure 11:
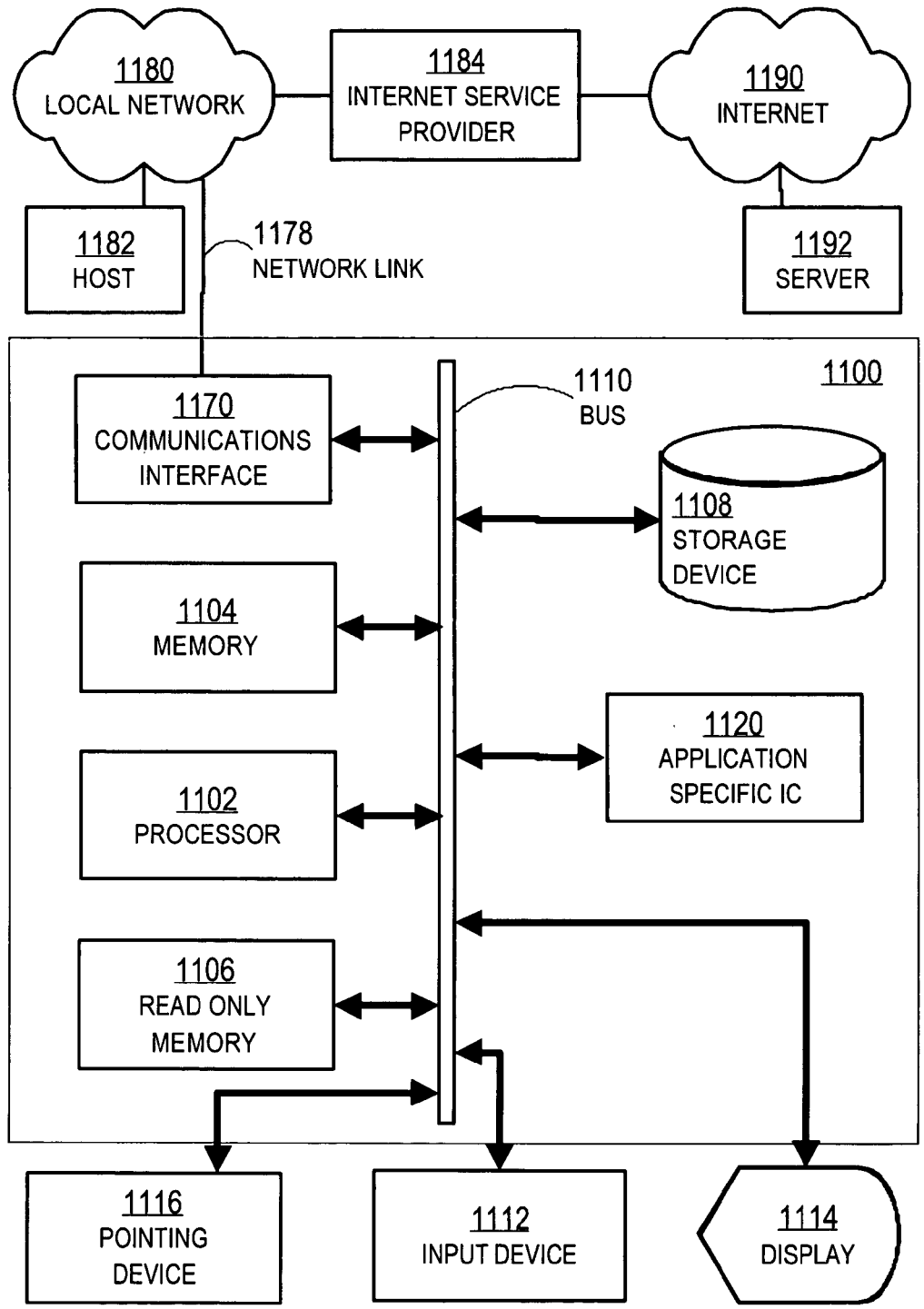
FIG. 11 is a block diagram that illustrates a computer system upon which an embodiment of the invention may be implemented.

FIG. 11 is a block diagram that illustrates a computer system 1100 upon which an embodiment of the invention may be implemented. Computer system 1100 includes a communication mechanism such as a bus 1110 for passing information between other internal and external components of the computer system 1100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 1110 includes many parallel conductors of information so that information is transferred quickly among devices coupled to the bus 1110. One or more processors 1102 for processing information are coupled with the bus 1110. A processor 1102 performs a set of operations on information. The set of operations include bringing information in from the bus 1110 and placing information on the bus 1110. The set of operations also typically include comparing two or more units of information, shifting positions of units of information, and combining two or more units of information, such as by addition or multiplication. A sequence of operations to be executed by the processor 1102 constitute computer instructions.

Computer system 1100 also includes a memory 1104 coupled to bus 1110. The memory 1104, such as a random access memory (RAM) or other dynamic storage device, stores information including computer instructions. Dynamic memory allows information stored therein to be changed by the computer system 1100. RAM allows a unit of information stored at a location called a memory address to be stored and retrieved independently of information at neighboring addresses. The memory 1104 is also used by the processor 1102 to store temporary values during execution of computer instructions. The computer system 1100 also includes a read only memory (ROM) 1106 or other static storage device coupled to the bus 1110 for storing static information, including instructions, that is not changed by the computer system 1100. Also coupled to bus 1110 is a non-volatile (persistent) storage device 1108, such as a magnetic disk or optical disk, for storing information, including instructions, that persists even when the computer system 1100 is turned off or otherwise loses power.

Information, including instructions, is provided to the bus 1110 for use by the processor from an external input device 1112, such as a keyboard containing alphanumeric keys operated by a human user, or a sensor. A sensor detects conditions in its vicinity and transforms those detections into signals compatible with the signals used to represent information in computer system 1100. Other external devices coupled to bus 1110, used primarily for interacting with humans, include a display device 1114, such as a cathode ray tube (CRT) or a liquid crystal display (LCD), for presenting images, and a pointing device 1116, such as a mouse or a trackball or cursor direction keys, for controlling a position of a small cursor image presented on the display 1114 and issuing commands associated with graphical elements presented on the display 1114.

In the illustrated embodiment, special purpose hardware, such as an application specific integrated circuit (IC) 1120, is coupled to bus 1110. The special purpose hardware is configured to perform operations not performed by processor 1102 quickly enough for special purposes. Examples of application specific ICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1100 also includes one or more instances of a communications interface 1170 coupled to bus 1110. Communication interface 1170 provides a two-way communication coupling to a variety of external devices that operate with their own processors, such as printers, scanners and external disks. In general the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. For wireless links, the communications interface 1170 sends and receives electrical, acoustic or electromagnetic signals, including infrared and optical signals, that carry information streams, such as digital data. Such signals are examples of carrier waves.

The term computer-readable medium is used herein to refer to any medium that participates in providing instructions to processor 1102 for execution. Such a medium may take many forms, including, but not limited to, non-volatile media, volatile media and transmission media. Non-volatile media include, for example, optical or magnetic disks, such as storage device 1108. Volatile media include, for example, dynamic memory 1104. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1178 typically provides information communication through one or more networks to other devices that use or process the information. For example, network link 1178 may provide a connection through local network 1180 to a host computer 1182 or to equipment 1184 operated by an Internet Service Provider (ISP). ISP equipment 1184 in turn provides data communication services through the public, world-wide packet-switching communication network of networks now commonly referred to as the Internet 1190. A computer called a server 1192 connected to the Internet provides a service in response to information received over the Internet. For example, server 1192 provides information representing video data for presentation at display 1114.

The invention is related to the use of computer system 1100 for implementing the techniques described herein. According to one embodiment of the invention, those techniques are performed by computer system 1100 in response to processor 1102 executing one or more sequences of one or more instructions contained in memory 1104. Such instructions, also called software and program code, may be read into memory 1104 from another computer-readable medium such as storage device 1108. Execution of the sequences of instructions contained in memory 1104 causes processor 1102 to perform the method steps described herein. In alternative embodiments, hardware, such as application specific integrated circuit 1120, may be used in place of or in combination with software to implement the invention. Thus, embodiments of the invention are not limited to any specific combination of hardware and software.

The signals transmitted over network link 1178 and other networks through communications interface 1170, which carry information to and from computer system 1100, are exemplary forms of carrier waves. Computer system 1100 can send and receive information, including program code, through the networks 1180, 1190 among others, through network link 1178 and communications interface 1170. In an example using the Internet 1190, a server 1192 transmits program code for a particular application, requested by a message sent from computer 1100, through Internet 1190, ISP equipment 1184, local network 1180 and communications interface 1170. The received code may be executed by processor 1102 as it is received, or may be stored in storage device 1108 or other non-volatile storage for later execution, or both. In this manner, computer system 1100 may obtain application program code in the form of a carrier wave.

Various forms of computer readable media may be involved in carrying one or more sequence of instructions or data or both to processor 1102 for execution. For example, instructions and data may initially be carried on a magnetic disk of a remote computer such as host 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to an infra-red signal, a carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1102 retrieves and executes the instructions using some of the data sent with the instructions. The instructions and data received in memory 1104 may optionally be stored on storage device 1108, either before or after execution by the processor 1102.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for delivering data for coordinating multiple party use of a facility, the method comprising the steps of:
producing with a processor conditions data by measuring with a device without human intervention a current condition of a facility for which use is coordinated among a plurality of human parties;
generating with a processor availability data that indicates availability for the facility based at least in part on the conditions data;
presenting for the plurality of parties coordination data based at least in part on the availability data;
determining a party who has access to the coordination data at a particular time, and
determining a particular level of privilege for a party to access sensitive coordination data among a plurality of levels of privilege based on an identity of the party, wherein a higher level of privilege provides access to more highly sensitive coordination data;
said step of generating availability data further comprises the steps of generating sensitive data, and
generating a plurality of views to present on a display with different levels of detail of the sensitive data in different views; and
said step of presenting the facility coordination data further comprises omitting a high-detail view of the plurality of views if the particular level of privilege is low.

2. The method as recited in claim 1, wherein:
the facility is at least one of a trauma center operating room, a surgical operating room, emergency room suites or a cardiac catheterization laboratory, or any combination thereof; and
the plurality of parties include a plurality of medical doctors, nurses, medical technicians or orderlies, or any combination thereof.

3. The method as recited in claim 1, wherein the facility is an aircraft and the plurality of parties include aircraft preparation personnel including a mechanic, a baggage handler, a caterer, cleaning crew member or a flight crew member, or any combination thereof.

4. The method as recited in claim 1, wherein the facility is a collection of emergency response facilities and the plurality of parties include a plurality of emergency response workers.

5. The method as recited in claim 1, said step of generating availability data further comprising the step of generating a value for a particular availability parameter and an estimate of accuracy for the value of the particular availability parameter.

6. The method as recited in claim 1, said step of generating availability data further comprising the step of predicting a particular future time for a particular subsequent stage of a sequence of stages for using the facility based at least in part on the conditions data.

7. The method as recited in claim 1, said step of producing conditions data further comprising collecting image data depicting at least a portion of the facility.

8. The method as recited in claim 7, wherein:
said step of generating availability data further comprises deriving from the image data a cartoon view comprising a solid filled shape to represent a feature apparent in the image data; and
said step of presenting the coordination data further comprises presenting the cartoon view instead of the image data.

9. The method as recited in claim 7, said step of generating availability data further comprising deriving from the image data a status value of a plurality of status values.

10. The method as recited in claim 9, wherein the plurality of status values comprises:
an empty status value that indicates an operating room table is not occupied and is not prepared for a new occupant;
a ready status value that indicates the operating room table is not occupied and is prepared for new occupant;
a drapes-off status value that indicates the operating room table is occupied and the occupant is not covered with a surgical drape; and
a drapes-on status value that indicates the operating room table is occupied and the occupant is covered with a surgical drape.

11. The method as recited in claim 1, said step of measuring current condition further comprising collecting equipment operation data that indicates operation of equipment utilized in the facility.

12. The method as recited in claim 11, said step of generating availability data further comprising deriving from the equipment operation data a status value of a plurality of status values.

13. The method as recited in claim 12, wherein the plurality of status values comprises:
a vital-signs-off status value that indicates patient vital signs are not detected by a vital signs monitor;
a vital-signs-on status value that indicates patient vital signs vital are detected by the vital signs monitor;
a pre-incision status value that indicates a surgeon has not started an incision with an electric tool; and
a post-incision status value that indicates a surgeon has started an incision with an electric tool.

14. The method as recited in claim 11, said step of collecting equipment operation data further comprising measuring at least one of electromagnetic radiation from the equipment and vibration radiation from the equipment.

15. The method as recited in claim 11, said step of collecting equipment operation data further comprising measuring electromagnetic radiation from a Bovie scalpel.

16. The method as recited in claim 1, wherein said step of presenting coordination data further comprises presenting a first progress bar for elapsed time based on the availability data, wherein the first progress bar overlaps and extends beyond a second bar that indicates time for a planned use.

17. The method as recited in claim 1, said step of presenting the coordination data further comprising integrating the coordination data with a tangible system for manually indicating current and planned use of the facility.

18. The method as recited in claim 1, wherein:
said step of determining a party who has access further comprises not detecting input from a party with a high level of privilege within a particular time interval; and
said step of presenting the facility coordination data further comprises omitting the high-detail view of the plurality of views.

19. A computer-readable storage medium storing one or more sequences of instructions for coordinating multiple party use of a facility, wherein execution of the one or more sequences of instructions by one or more processors causes the one or more processors to perform the steps of:

receiving conditions data measured with a device without human intervention, wherein the conditions data indicates current condition of a facility that is used by a plurality of human parties;

generating availability data that indicates availability for the facility based at least in part on the conditions data;

presenting for the plurality of parties coordination data based at least in part on the availability data;

determining a party who has access to the coordination data at a particular time, and determining a particular level of privilege for a party to access sensitive coordination data among a plurality of levels of privilege based on an identity of the party, wherein a higher level of privilege provides access to more highly sensitive coordination data;

said step of generating availability data further comprises the steps of generating sensitive data, and generating a plurality of views to present on a display with different levels of detail of the sensitive data in different views; and said step of presenting the facility coordination data further comprises omitting a high-detail view of the plurality of views if the particular level of privilege is low.

20. An apparatus comprising:
a processor; and
a computer-readable medium,
wherein the computer-readable medium carries instructions, which when executed by the processor, cause the apparatus to receive conditions data measured with a device without human intervention, wherein the conditions data indicates current condition of a facility that is used by a plurality of human parties;

generate availability data that indicates availability for the facility based at least in part on the conditions data;

present for the plurality of parties coordination data based at least in part on the availability data;

determine a party who has access to the coordination data at a particular time, and determine a particular level of privilege for a party to access sensitive coordination data among a plurality of levels of privilege based on an identity of the party, wherein a higher level of privilege provides access to more highly sensitive coordination data;

wherein to generate availability data further comprises
to generate sensitive data, and
to generate a plurality of views to present on a display with different levels of detail of the sensitive data in different views; and wherein to present the facility coordination data further comprises to omit a high-detail view of the plurality of views if the particular level of privilege is low.

* * * * *